(12) United States Patent
Freedman et al.

(10) Patent No.: US 12,071,626 B2
(45) Date of Patent: Aug. 27, 2024

(54) SPLICE-SWITCHING OLIGONUCLEOTIDES AND METHODS OF USE

(71) Applicant: Duke University, Durham, NC (US)

(72) Inventors: Jennifer Freedman, Durham, NC (US); Brendon Patierno, Durham, NC (US); Bonnie LaCroix, Durham, NC (US); Timothy Robinson, Durham, NC (US); Bruce Sullenger, Durham, NC (US); Daniel George, Durham, NC (US); Steven Patierno, Durham, NC (US)

(73) Assignee: Duke University, Durham, NC (US)

( * ) Notice: Subject to any disclaimer, the term of this patent is extended or adjusted under 35 U.S.C. 154(b) by 8 days.

(21) Appl. No.: 17/464,474

(22) Filed: Sep. 1, 2021

(65) Prior Publication Data

US 2021/0395754 A1    Dec. 23, 2021

Related U.S. Application Data

(63) Continuation of application No. 15/773,841, filed as application No. PCT/US2016/060549 on Nov. 4, 2016, now Pat. No. 11,136,584.

(60) Provisional application No. 62/274,427, filed on Jan. 4, 2016, provisional application No. 62/250,713, filed on Nov. 4, 2015.

(51) Int. Cl.

| C12N 15/11 | (2006.01) |
|---|---|
| A61K 31/7105 | (2006.01) |
| A61K 31/7125 | (2006.01) |
| A61K 45/06 | (2006.01) |
| A61P 35/00 | (2006.01) |
| C07H 21/04 | (2006.01) |
| C12N 15/113 | (2010.01) |
| A61K 48/00 | (2006.01) |

(52) U.S. Cl.
CPC ...... *C12N 15/1138* (2013.01); *A61K 31/7105* (2013.01); *A61K 31/7125* (2013.01); *A61K 45/06* (2013.01); *A61P 35/00* (2018.01); *C07H 21/04* (2013.01); *C12N 15/11* (2013.01); *C12N 15/1136* (2013.01); *A61K 48/0066* (2013.01); *C12N 2310/11* (2013.01); *C12N 2310/315* (2013.01); *C12N 2310/321* (2013.01); *C12N 2320/31* (2013.01); *C12N 2320/33* (2013.01)

(58) Field of Classification Search
None
See application file for complete search history.

(56) References Cited

U.S. PATENT DOCUMENTS

| 5,914,269 A | 6/1999 | Bennett |
|---|---|---|
| 5,976,879 A | 11/1999 | Kole |
| 2003/0194704 A1 | 10/2003 | Penn |
| 2007/0009899 A1 | 1/2007 | Mounts |
| 2007/0039076 A1 | 2/2007 | Boukharov |
| 2012/0237935 A1 | 9/2012 | Xu |
| 2012/0283120 A1 | 11/2012 | Watanabe |
| 2014/0031409 A1 | 1/2014 | Worm |
| 2014/0142160 A1 | 5/2014 | Lee |
| 2014/0206748 A1 | 7/2014 | Dehm |
| 2015/0232839 A1 | 8/2015 | Iversen |

FOREIGN PATENT DOCUMENTS

| WO | 2011056894 A2 | 5/2011 |
|---|---|---|
| WO | 2014052613 A2 | 4/2014 |

OTHER PUBLICATIONS

Maeda, et al., Cadherin switching: essential for behavioral but not morphological changes during an epithelium-to-mesenchyme transition. J Cell Sci, 2005. 118(Pt 5): p. 873-87.
Mani, et al., The epithelial-mesenchymal transition generates cells with properties of stem cells. Cell, 2008. 133(4): p. 704-15.
McNamara, et al., Cell type-specific delivery of siRNAs with aptamer-siRNA chimeras. Nat Biotechnol, 2006. 24(8): p. 1005-15.
Mellinghoff, et al., HER2/neu kinase-dependent modulation of androgen receptor function through effects on DNA binding and stability. Cancer Cell, 2004. 6: p. 517-27.
Mulholland, et al., Cell autonomous role of PTEN in regulating castration-resistant prostate cancer growth. Cancer Cell, 2011. 19(6): p. 792-804.
Mulholland, et al., Pten loss and RAS/MAPK activation cooperate to promote EMT and metastasis initiated from prostate cancer stem/progenitor cells. Cancer Res, 2012. 72(7): p. 1878-89.
Neff, et al., An aptamer-siRNA chimera suppresses HIV-1 viral loads and protects from helper CD4(+) T cell decline in humanized mice. Sci Transl Med, 2011. 3(66): p. 66ra6.
Ni, et al., Prostate-targeted radiosensitization via aptamer-shRNA chimeras in human tumor xenografts. J Clin Invest, 2011. 121(6): p. 2383-90.
Nishi, et al., Changes in gene expression of growth factors and their receptors during castration-induced involution and androgen-induced regrowth of rat prostates. Prostate, 1996. 28(3): p. 139-52.
Paez-Ribes, et al., Antiangiogenic therapy elicits malignant progression of tumors to increased local invasion and distant metastasis. Cancer Cell, 2009. 15(3): p. 220-31.
Pastor, et al., Induction of tumour immunity by targeted inhibition of nonsense-mediated mRNA decay. Nature, 2010. 465(7295): p. 227-30.
Roberts, et al., Efficient and persistent splice switching by systemically delivered LNA oligonucleotides in mice. Mol Ther, 2006. 14(4): p. 471-5.
Ryan, et al., Phase II study of abiraterone acetate in chemotherapy-naive metastatic castration-resistant prostate cancer displaying bone flare discordant with serologic response. Clin Cancer Res, 2011. 17(14): p. 4854-61.

(Continued)

*Primary Examiner* — Ekaterina Poliakova-Georgantas
*Assistant Examiner* — Ekaterina Poliakova
(74) *Attorney, Agent, or Firm* — Nutter McClennen & Fish LLP

(57) ABSTRACT

The present disclosure provides methods and compositions for the treatment of cancer. In some aspects, the present disclosure provides splice-switching oligonucleotides that downregulate AR or EGFR expression and methods of using these splice-switching oligonucleotides to treat cancer.

29 Claims, 12 Drawing Sheets

Specification includes a Sequence Listing.

(56) References Cited

OTHER PUBLICATIONS

Saha, et al., Overexpression of E-cadherin and beta-catenin proteins in metastatic prostate cancer cells in bone. Prostate, 2008. 68(1): p. 78-84.
Salgia, et al., A phase I study of XL184, a RET, VEGFR2, and MET kinase inhibitor, in patients (pts) with advanced malignancies, including pts with medullary thyroid cancer (MTC), in Journal of Clinical Oncology 26S 2008: ASCO 2008 Annual Meeting, abstract 3522.
Sazani, et al., Nuclear antisense effects of neutral, anionic and cationic oligonucleotide analogs. Nucleic Acids Res, 2001. 29(19): p. 3965-74.
Sazani, et al., Systemically delivered antisense oligomers upregulate gene expression in mouse tissues. Nat Biotechnol, 2002. 20(12): p. 1228-33.
Smith, et al., Comparison of Biosequences. Adv. Appl. Math., 1981, 2, 482-489.
Sun, et al., Androgen deprivation causes epithelial-mesenchymal transition in the prostate: implications for androgen-deprivation therapy. Cancer Res, 2012. 72(2): p. 527-36.
Sun, et al., Castration resistance in human prostate cancer is conferred by a frequently occurring androgen receptor splice variant. J Clin Invest, 2010. 120(8): p. 2715-30.
Sztainberg, et al., Reversal of phenotypes in MECP2 duplication mice using genetic rescue or antisense oligonucleotides. Nature, 2015. 528(7580): p. 123-6.
Tanaka, et al., Monoclonal antibody targeting of N-cadherin inhibits prostate cancer growth, metastasis and castration resistance. Nat Med, 2010. 16(12): p. 1414-20.
Taylor, et al., Integrative genomic profiling of human prostate cancer. Cancer Cell, 2010. 18(1): p. 11-22.
Tomita, et al., Cadherin switching in human prostate cancer progression. Cancer Res, 2000. 60(13): p. 3650-4.
Veedu, et al., Locked nucleic acids: promising nucleic acid analogs for therapeutic applications. Chem Biodivers, 2010. 7(3): p. 536-42.
Verras, et al., The androgen receptor negatively regulates the expression of c-MET: implications for a novel mechanism of prostate cancer progression. Cancer Res, 2007. 67(3) p. 967-75. v.
Vo-Dinh, et al., SERS nanosensors and nanoreporters: golden opportunities in biomedical applications. Wiley Interdiscip Rev Nanomed Nanobiotechnol, 2015. 7(1): p. 17-33.
Wan, et al., Activation of beta-catenin signaling in androgen receptor-negative prostate cancer cells. Clin Cancer Res, 2012. 18(3): p. 726-36.
Wang et al., A 90 kDa fragment of filamin A promotes Casodex-induced growth inhibition in Casodex-resistant androgen receptor positive C4-2 prostate cancer cells. Oncogene, 2007. 26(41): p. 6061-70.
Wang, et al., PRL-3 down-regulates PTEN expression and signals through PI3K to promote epithelial-mesenchymal transition. Cancer Res, 2007. 67(7): p. 2922-6.
Watson, et al., Constitutively active androgen receptor splice variants expressed in castration-resistant prostate cancer require full-length androgen receptor. Proc Natl Acad Sci USA, 2010. 107(39): p. 16759-65.
Wheeler, et al., Inhibition of HIV transmission in human cervicovaginal explants and humanized mice using CD4 aptamer-siRNA chimeras. J Clin Invest, 2011. 121(6): p. 2401-12.
Wissner, et al., The development of HKI-272 and related compounds for the treatment of cancer. Arch Pharm Chem Life Sci, 2008. 341: p. 465-77.
Witta, et al., Restoring E-cadherin expression increases sensitivity to epidermal growth factor receptor inhibitors in lung cancer cell lines. Cancer Res, 2006. 66(2): p. 944-50.
Yakes, et al., Cabozantinib (XL184), a novel MET and VEGFR2 inhibitor, simultaneously suppresses metastasis, angiogenesis, and tumor growth. Mol Cancer Ther, 2011.
Zanetta, et al., Molecular therapeutic strategies for spinal muscular atrophies: current and future clinical trials. Clin Ther, 2014. 36(1): p. 128-40.
Zhang, et al., PowerBlast: A new network blast application for interactive or automated sequence analysis and annotation, Genome Res., 1997, 7, 649-656.
Zhau, et al., Epithelial to mesenchymal transition (EMT) in human prostate cancer: lessons learned from ARCaP model. Clin Exp Metastasis, 2008. 25(6): p. 601-10.
Zhou, et al., Novel dual inhibitory function aptamer-siRNA delivery system for HIV-1 therapy. Mol Ther, 2008: 16(8): p. 1481-9.
Zhu, et al., Role of androgens and the androgen receptor in epithelial-mesenchymal transition and invasion of prostate cancer cells. FASEB J, 2010. 24(3): p. 769-77.
Abrens-Fath, et al., Androgen receptor function is modulated by the tissue-specific AR45 variant. FEBS J, 2005. 272 (1): p. 74-84.
Aftab, et al., MET and VEGF: synergistic targets in castration-resistant prostate cancer. Clin Transl Oncol, 2011. 13 (10): p. 703-9.
Altschul, et al., Basic local alignment search tool. J. Mol. Biol., 1990, 215, 403-410.
Armstrong, et al., Circulating tumor cells from patients with advanced prostate and breast cancer display both epithelial and mesenchymal markers. Mol Cancer Res, 2011. 9(8): p. 997-1007.
Bates, et al., Discovery and development of the G-rich oligonucleotide AS1411 as a novel treatment for cancer. Exp Mol Pathol, 2009. 86(3): p. 151-64.
Bauman, et al., Anti-tumor activity of splice-switching oligonucleotides. Nucleic Acids Res, 2010. 38(22): p. 8348-56.
Bauman, et al., Therapeutic potential of splice-switching oligonucleotides. Oligonucleotides, 2009. 19(1): p. 1-13.
Birchmeier, et al., Met, metastasis, motility, and more. Nat Rev Mol Cell Biol, 2003. 4(12): p. 915-25.
Carver, et al., Reciprocal feedback regulation of P13K and androgen receptor signaling in PTEN-deficient prostate cancer. Cancer Cell, 2011. 19(5): p. 575-86.
Celia-Terrassa, et al., Epithelial-mesenchymal transition can suppress major attributes of human epithelial tumor-initiating cells. J Clin Invest, 2012. 122(5): p. 1849-68.
Chao, et al., Hepatocyte induced re-expression of E-cadherin in breast and prostate cancer cells increases chemoresistance. Clio Exp Metastasis, 2012. 29(1): p. 39-50.
Chono, et al., An efficient and low immunostimulatory nanoparticle formulation for systemic siRNA delivery to the tumor. J Control Release, 2008. 131(1): p. 64-9.
Christensen, et al., c-Met as a target for human cancer and characterization of inhibitors for therapeutic intervention. Cancer Lett, 2005. 225(I): p. 1-26.
Cleutjens, et al., Two androgen response regions cooperate in steroid hormone regulated activity of the prostate-specific antigen promoter. J Biol Chem, 1996. 271(11): p. 6379-88.
Contreras, et al., The expression of syndecan-1 and -2 is associated with Gleason score and epithelial-mesenchymal transition markers, E-cadherin and beta-catenin, in prostate cancer. Urol Oncol, 2010. 28(5): p. 534-40.
Dahlman, et al., Modulators of prostate cancer cell proliferation and viability identified by short-hairpin RNA library screening. PLoS ONE, 2012. 7(4): p. 1-9.
Dassie, et al., Systemic administration of optimized aptamer-siRNA chimeras promotes regression of PSMA-expressing tumors. Nat Biotechnol, 2009. 27(9): p. 839-49.
Dehm, et al., Splicing of a novel androgen receptor exon generates a constitutively active androgen receptor that mediates prostate cancer therapy resistance. Cancer Res, 2008. 68(13):p. 5469-77.
Ding, et al., SMAD4-dependent barrier constrains prostate cancer growth and metastatic progression. Nature, 2011. 470(7333): p. 269-73.
Ebos, et al., Accelerated metastasis after short-term treatment with a potent inhibitor of tumor angiogenesis. Cancer Cell, 2009. 15(3): p. 232-9.
Flanagan, et al., A cytosine analog that confers enhanced potency to antisense oligonucleotides. 1999, Proc. Natl. Acad. Sci. 96:3513.
Genbank submission JT222415.1 (Nov. 7, 2012) Retrieved on Mar. 20, 2017 from https://www.ncbi.nlm.nih/nuccore/GI:375498133.

(56) References Cited

OTHER PUBLICATIONS

Genbank submission KA111089.1 (Nov. 5, 2012) Retrieved on Mar. 20, 2017 from https://www.ncbi.nlm.nih/nuccore/GI:401489355.

Ghosh, et al., Signal transduction pathways in androgen-dependent and -independent prostate cancer cell proliferation. Endocr Reial Cancer, 2005. 12(1): p. 119-34.

Ginisty, et al., Structure and functions of nucleolin. J Cell Sci, 1999. 112(Pt 6): p. 761-72.

Grasso, et al., ErbB kinases and NDF signaling in human prostate cancer cells. Oncogene, 1997. 15:p. 2705-16.

Gravdal, et al., A switch from E-cadherin to N-cadherin expression indicates epithelial to mesenchymal transition and is of strong and independent importance for the progress of prostate cancer. Clin Cancer Res, 2007. 13(23): p. 7003-11.

Guo, et al., A novel androgen receptor splice variant is up-regulated during prostate cancer progression and promotes androgen depletion-resistant growth. Cancer Res, 2009. 69(6): p. 2305-13.

Gupta, et al., Identification of selective inhibitors of cancer stem cells by high-throughput screening. Cell. 2009. 138 (4): p. 645-59.

Holmes, et al., Steric inhibition of human immunodeficiency virus type-1 Tat-dependent trans-activation in vitro and in cells by oligonucleotides containing 2'-O-methyl G-clamp ribonucleoside analogues. 2003, Nucleic Acids Res. 31:2759.

Hong, et al., AZD9150, a next-generation antisense oligonucleotide inhibitor of STAT3 with early evidence of clinical activity in lymphoma and lung cancer. Sci Transl Med, 2015. 7(314): p. 314ra185.

Hornberg, et al., Expression of androgen receptor splice variants in prostate cancer bone metastases is associated with castration-resistance and short survival PLoS One, 2011. 6(4): p. e19059.

Hu, et al., Distinct transcriptional programs mediated by the ligand-dependent full-length androgen receptor and its splice variants in castration-resistant prostate cancer. Cancer Res. Jun. 18, 2012.

Hu, et al., Ligand-independent androgen receptor variants derived from splicing of cryptic exons signify hormone-refractory prostate cancer. Cancer Res, 2009. 69(1): p. 16-22.

Humphrey, et al., Hepatocyte growth factor and its receptor (c-MET) in prostatic carcinoma. American Journal of Pathology, 1995. 147(2): p. 386-96.

Hussain, et al., Cabozantinib (XL184) in metastatic castration-resistant prostate cancer (mCRPC): Results from a phase II randomized discontinuation trial, in Journal of Clinical Oncology 29S 201 I: ASCO 2011 Annual Meeting, abstract 4516.

International Searching Authority. International Search Report and Written Opinion for application PCT/US2016/060549. dated Apr. 18, 2017. 13 pages.

Jathal, el al., Targeting ErbB3: the new RTK(id) of the prostate cancer block. Immunol Endocr Metab Agents Med Chem, 2011. 11: p. 131-49.

Jennbacken, et al., N-cadherin increases after androgen deprivation and is associated with metastasis in prostate cancer. Endocr Relat Cancer, 2010. 17(2): p. 469-79.

Jennbacken, et al., Prostate cancer progression into androgen independency is associated with alterations in cell adhesion and invasivity. Prostate, 2006. 66(15): p. 1631-40.

Jenster, et al., Domains of the human androgen receptor involved in steroid binding, transcriptional activation, and subcellular localization. Mol Endocrinol, 1991. 5(10): p. 1396-404.

Josson, et al., B2-microglobulin induces epithelial to mesenchymal transition and confers cancer lethality and bone metastasis in human cancer cells. Cancer Res, 2011. 71(7): p. 2600-10.

Kalluri, et al., Epithelial-mesenchymal transition and its implications for fibrosis. J Clin Invest, 2003. 112(12): p. 1776-84.

Kole, et al., Exon skipping therapy for Duchenne muscular dystrophy. Adv Drug Deliv Rev, 2015. 87: p. 104-7.

Kong, et al., Epithelial to mesenchymal transition is mechanistically linked with stem cell signatures in prostate cancer cells. PLoS One, 2010. 5(8): e12445.

Kotula, et al., Aptamer-mediated delivery of splice-switching oligonucleotides to the nuclei of cancer cells. Nucleic Acid Ther, 2012. 22(3): p. 187-95.

Lentz, et al., Rescue of hearing and vestibular function by antisense oligonucleotides in a mouse model of human deafness. Nat Med, 2013. 19(3): p. 345-50.

Li, et al., Efficient gene silencing in metastatic tumor by siRNA formulated in surface-modified nanoparticles. J Control Release, 2008. 126(1): p. 77-84.

Li, et al., Efficient oncogene silencing and metastasis inhibition via systemic delivery of siRNA. Mol Ther, 2008. 16 (5): p. 942-6.

Lin, et al., The phosphatidylinositol 3'-kinase pathway is a dominant growth factor-activated cell survival pathway in LNCaP human prostate carcinoma cells. Cancer Res, 1999. 59(12)': p. 2891-7.

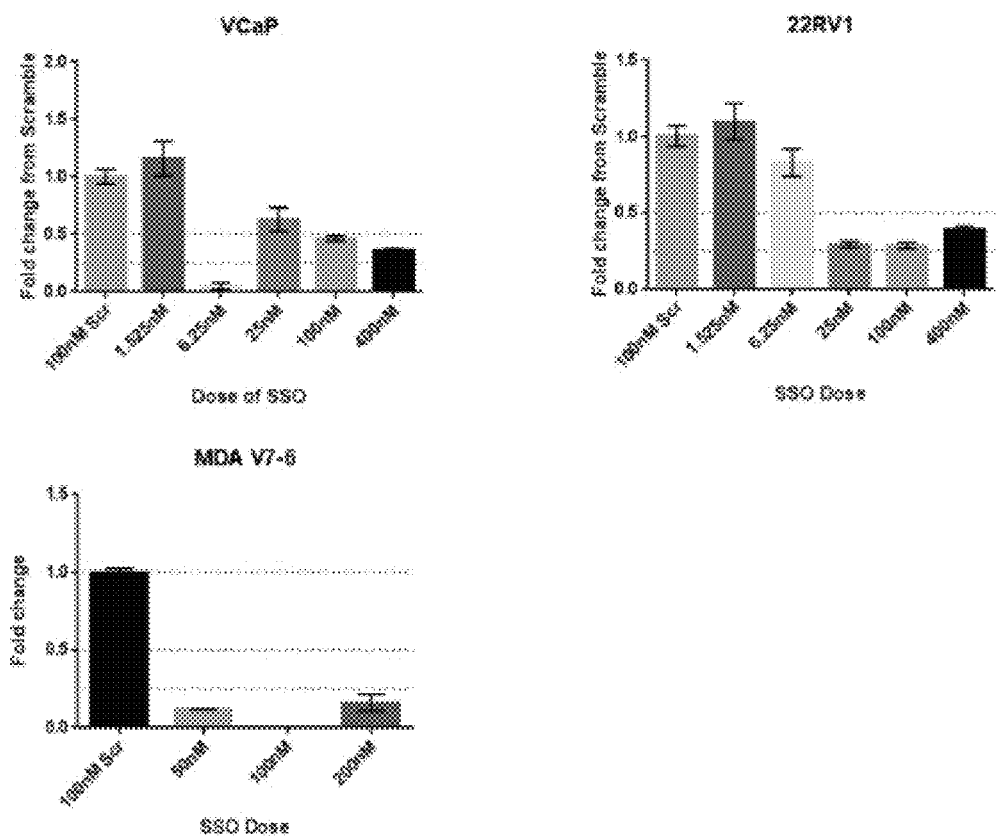
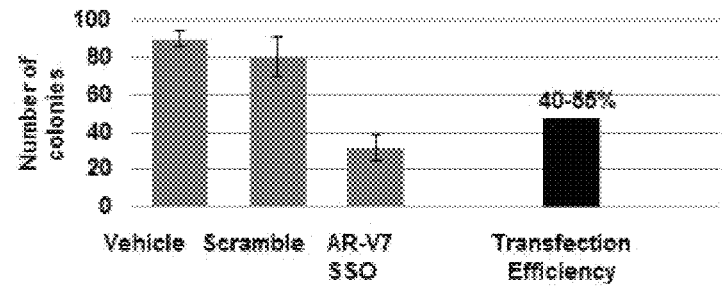
Figure 4B-C

SPLICE-SWITCHING OLIGONUCLEOTIDES AND METHODS OF USE

CROSS-REFERENCE TO RELATED APPLICATIONS

This application is a continuation of U.S. application Ser. No. 15/773,841 filed on May 4, 2018, which represents the national stage entry of International Application PCT/US2016/060549 filed Nov. 4, 2016, which claims priority to U.S. Provisional Application No. 62/250,713 filed Nov. 4, 2015 and U.S. Provisional Application No. 62/274,427 filed Jan. 4, 2016, the contents of which are incorporated by reference in their entireties.

STATEMENT REGARDING FEDERALLY SPONSORED RESEARCH

This invention was made with Government support under Federal Grant no. W81XWH-14-1-0569 awarded by the Army Medical Research and Materiel Command (ARMY/MRMC). The Federal Government has certain rights to this invention.

REFERENCE TO A SEQUENCE LISTING SUBMITTED VIA EFS-WEB

This application includes an electronically submitted Sequence Listing in .txt format. The .txt file contains a sequence listing entitled 155554_00612_ST25.txt" and was created on Aug. 30, 2021, and is 3.77 kbytes in size. The Sequence Listing contained in this .txt file is part of the specification and is hereby incorporated herein in its entirety.

BACKGROUND OF THE INVENTION

Prostate cancer is the second leading cause of cancer-related deaths in the US among men, with 220,800 new cases and 27,540 deaths estimated to occur in 2015. Previous work from our laboratory and others has revealed oncogenic signaling pathways contributing to aggressive disease, including androgen receptor (AR) and epidermal growth factor receptor (EGFR). The androgen receptor (AR) is a steroid hormone receptor that plays a crucial role in the development of normal prostate tissue, as well as in the progression of prostate cancer. Patients with metastatic disease are initially treated with androgen deprivation therapy.

African American (AA) men exhibit a nearly 2-fold higher incidence and 3-fold higher mortality rate from prostate cancer compared to white men and disparities in tumor aggressiveness remain after controlling for social determinants of health. Previous work from our laboratory and others has revealed differences in gene expression that contribute to prostate cancer health disparities among AAs. Oncogenic signaling pathways exhibiting up-regulation more often in AA prostate cancer include androgen receptor (AR) and epidermal growth factor receptor (EGFR). Thus, novel therapeutic strategies capable of driving production of inhibitory AR and EGFR isoforms and capable of limiting aberrant constitutively active AR isoforms are urgently needed. Such strategies will increase our understanding of these molecular mechanisms underlying prostate cancer in AA men. In addition, such strategies provide novel specific approaches for treatment that will help reduce prostate cancer disparities for AAs and will improve treatment of advanced stage disease in all men with aggressive disease driven by these mechanisms.

SUMMARY OF THE INVENTION

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims herein for interpreting the scope of the invention.

In one aspect, the disclosure provides a splice-switching oligonucleotide comprising, consisting essentially of, consisting of or is a sequence complementary to the region comprising the 5' splice site of Exon 1 or Exon CE3 of the androgen receptor (AR) or a sequence complementary to the region comprising exon 16 or exon 18 of the epithelial growth factor receptor (EGFR). In one aspect, the oligonucleotide comprises, consisting essentially of, consists of or is a sequence that is complementary to SEQ ID NO: 1. In another aspect, the oligonucleotide comprises, consists essentially of, consists of or is SEQ ID NO: 3. In yet another aspect, the oligonucleotide comprises, consists essentially of, consists of or is a sequence that is complementary to SEQ ID NO: 2. In yet a further aspect, splice-switching oligonucleotide o comprises, consists essentially of, consisting of or is SEQ ID NO: 4.

In another aspect, the oligonucleotide comprises, consists essentially of, consists of or is a sequence complementary to the region comprising exon 16 of the epithelial growth factor receptor (EGFR). In yet another aspect, the oligonucleotide comprises, consists essentially of, consists of or is SEQ ID NO: 5. In yet another aspect, the oligonucleotide comprises, consists essentially of, consists of or is SEQ ID NO: 6.

In yet another aspect, the disclosure provides a splice-switching oligonucleotide that can reduce expression of androgen receptor or EGFR in a cancer cell.

In another aspect, the disclosure provides a method of treating a subject suffering from a disease comprising, consisting essentially of, or consisting of administering to the subject a therapeutically effective amount of a splice-switching oligonucleotide or composition described herein such that the disease is treated. In yet another aspect, the disease is cancer, preferably prostate cancer.

In yet another aspect, a method of treating a subject suffering from a cancer is provided. The method comprises, consists essentially of, or consists of administering to the subject a therapeutically effective amount of a composition comprising a splice-switching oligonucleotide and a second cancer therapy in an amount effective to treat the cancer.

In yet a further aspect, a kit for treating cancer is provided. The kit comprises, consists essentially of, or consists of at least one splice-switching oligonucleotide (SSO) described herein. In some aspects, the kit further comprises a second cancer therapy.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims herein for interpreting the scope of the invention.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 4B are graphs depicting AR-V7 SSO inhibiting AR-V7 RNA in VCaP and 22Rv1 prostate cancer cells derived from a white prostate cancer patient and in MDA PCa 2b prostate cancer cells derived from an African American prostate cancer patient.

FIG. 4C is a graph depicting AR-V7 SSO inhibiting colony forming ability in MDA PCa 2b prostate cancer cells derived from an African American prostate cancer patient.

DETAILED DESCRIPTION OF THE INVENTION

Figure 1:
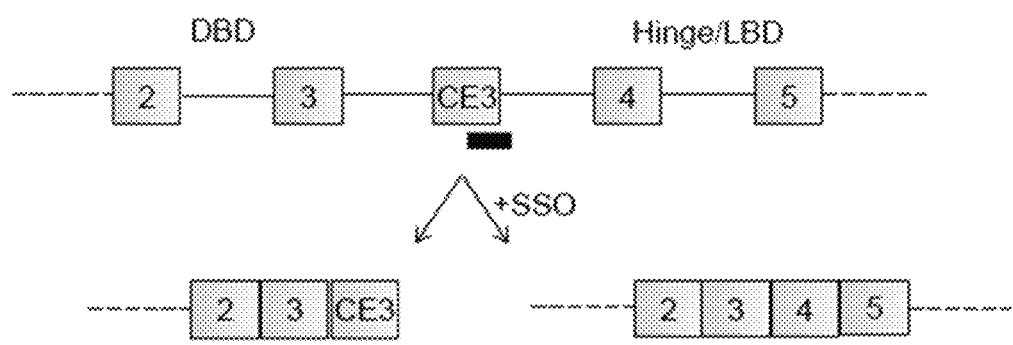
FIG. 1 is a cartoon showing splicing of AR that leads to the production of constitutively active AR variant AR-V7. Aberrant usage of the splice site of exon CE3 leads to its inclusion, premature termination and generation of AR-V7 (left). The SSO blocks the splice site of exon CE3 leading to production of wild type AR (right). DBD=DNA-binding domain, LDB=ligand-binding domain.
Figure 2:
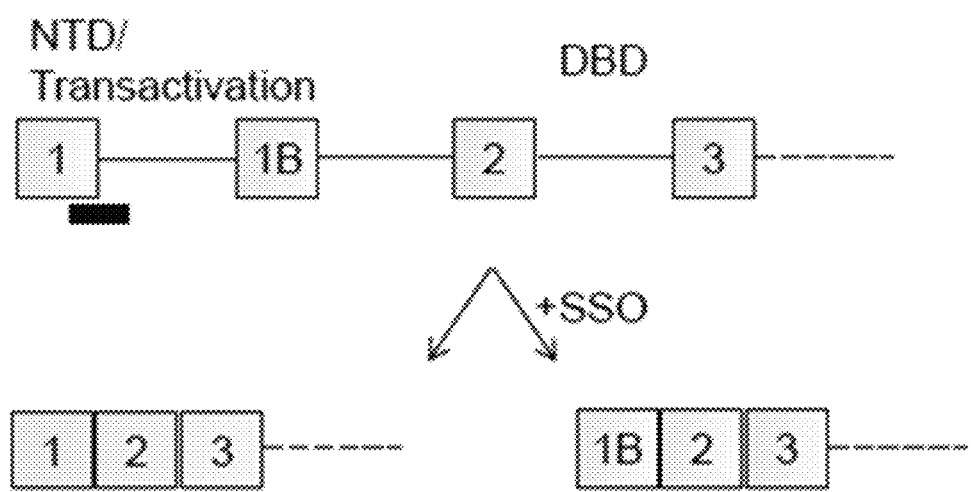
FIG. 2 is a cartoon depiction of splicing generating AR45. Normal splicing of AR pre-mRNA leads to production of wild type AR (left). SSO drives the production of the dominant-negative AR45 variant (right). The SSO blocks the splice site of exon 1 leading to inclusion of exon 1B and thus production of the dominant-negative AR45 variant. NTD=N-terminal domain, DBD=DNA-binding domain.

The present invention has been described in terms of one or more preferred embodiments, and it should be appreciated that many equivalents, alternatives, variations, and modifications, aside from those expressly stated, are possible and within the scope of the invention.

The present invention relates to methods and compositions for controlling expression of androgen receptor (AR) and Epidermal Growth Factor Receptor (EGFR) using compounds that modulate splicing of pre-mRNA encoding these receptors. In a preferred embodiment, the compounds are splice-switching oligonucleotides or splice switching oligomers (SSOs).

Splice-switching oligonucleotides represent a novel therapeutic strategy to combat aggressive prostate cancer. Unlike standard RNA interference to inhibit the expression of a gene, SSOs simultaneously limit the production of pathogenic proteins and induce the expression of protein variants with therapeutic value. SSOs modulate pre-mRNA splicing by binding to target pre-mRNAs and blocking access of the splicing machinery to a particular splice site, and can be used to produce novel splice variants, correct aberrant splicing or manipulate alternative splicing.

The following terms are used herein:

"About" is used to provide flexibility to a numerical range endpoint by providing that a given value may be "slightly above" or "slightly below" the endpoint without affecting the desired result.

As used herein, "treatment" or "treating" refers to the clinical intervention made in response to a disease, disorder or physiological condition manifested by a patient or to which a patient may be susceptible. The aim of treatment includes the alleviation or prevention of symptoms, slowing or stopping the progression or worsening of a disease, disorder, or condition and/or the remission of the disease, disorder or condition. Specifically, treatment results in the reduction in tumor load or volume in the patient, and in some instances, leads to regression and elimination of the tumor or tumor cells. As used herein, the term "treatment" is not necessarily meant to imply cure or complete abolition of the tumor. Treatment may refer to the inhibiting or slowing of the progression of the tumor, reducing the incidence of tumor, reducing metastasis of the tumor, or preventing additional tumor growth. In some embodiments, treatment results in complete regression of the tumor.

By "ameliorate," "amelioration," "improvement" or the like we mean a detectable improvement or a detectable change consistent with improvement occurs in a subject or in at least a minority of subjects, e.g., in at least about 2%, 5%, 10%, 15%, 20%, 25%, 30%, 40%, 50%, 60%, 70%, 75%, 80%, 85%, 90%, 95%, 98%, 100% or in a range about between any two of these values. Such improvement or change may be observed in treated subjects as compared to subjects not treated with the compositions of the present invention, where the untreated subjects have, or are subject to developing, the same or similar tumor.

The term "effective amount" or "therapeutically effective amount" refers to an amount sufficient to effect beneficial or desirable biological and/or clinical results.

The term "disease" as used herein includes, but is not limited to, any abnormal condition and/or disorder of a structure or a function that affects a part of an organism. It may be caused by an external factor, such as an infectious disease, or by internal dysfunctions, such as cancer, autoimmune diseases and the like. The preferred disease to be treated by the oligonucleotides, compositions and methods herein are diseases that results from or are associated with an increased expression of AR or EGFR, for example, cancer.

As is known in the art, a "cancer" or "tumor" is generally considered as uncontrolled cell growth. The terms "cancer" and "tumor" are used herein interchangeably. The methods of the present invention can be used to treat any cancer including, but not limited to, carcinoma, lymphoma, blastoma, sarcoma, and leukemia. More particular examples of such cancers include breast cancer, prostate cancer, colon cancer, squamous cell cancer, small-cell lung cancer, non-small cell lung cancer, ovarian cancer, cervical cancer, gastrointestinal cancer, pancreatic cancer, glioblastoma, liver cancer, bladder cancer, hepatoma, colorectal cancer, uterine cervical cancer, endometrial carcinoma, salivary gland carcinoma, mesothelioma, kidney cancer, vulval cancer, pancreatic cancer, thyroid cancer, hepatic carcinoma, skin cancer, melanoma, brain cancer, neuroblastoma, myeloma, various types of head and neck cancer, acute lymphoblastic leukemia, acute myeloid leukemia, Ewing sarcoma and peripheral neuroepithelioma. In certain embodiments, the cancer is prostate cancer.

As used herein, the terms "subject" and "patient" are used interchangeably herein and refer to both human and nonhuman animals. The term "nonhuman animals" of the disclosure includes all vertebrates, e.g., mammals and non-mammals, such as nonhuman primates, sheep, dog, cat, horse, cow, chickens, amphibians, reptiles, and the like. Preferably, the subject is a human patient that is suffering from cancer (e.g., prostate cancer). In a preferred embodiment, the patient is suffering from an aggressive form of the cancer, for example an aggressive form of prostate cancer. In one embodiment, the subject is preferably an African American male suffering from prostate cancer.

As used herein, the term "altering the splicing of a pre-mRNA" refers to altering the splicing of a cellular pre-mRNA target resulting in an altered ratio of spliced products. Such an alteration of splicing can be detected by a variety of techniques well known to one of skill in the art. For example, RT-PCR can be used on total cellular RNA to detect the ratio of splice products in the presence and the absence of an SSO.

As used herein, the term "complementary" is used to indicate a sufficient degree of complementarity or precise pairing such that stable and specific binding occurs between an oligonucleotide and a DNA or RNA containing the target sequence. It is understood in the art that the sequence of an oligonucleotide need not be 100% complementary to that of its target. For example, for an SSO there is a sufficient degree of complementarity when, under conditions which permit splicing, binding to the target will occur and non-specific binding will be substantially avoided. Moreover, an oligonucleotide may hybridize over one or more segments such that intervening or adjacent segments are not involved in the hybridization event (e.g., a loop structure, mismatch or hairpin structure). The SSOs of the present invention comprise at least 70%, or at least 75%, or at least 80%, or at least 85%, or at least 90%, or at least 92%, or at least 95%, or at least 97%, or at least 98%, or at least 99%, or at least 100% sequence complementarity to a target region within the target nucleic acid sequence to which they are targeted. For example, a SSO in which 18 of 20 nucleobases of the SSO are complementary to a target region, and would therefore specifically hybridize, would represent 90 percent complementarity. In this example, the remaining non-complementary nucleobases may be clustered or interspersed with complementary nucleobases and need not be contiguous to each other or to complementary nucleobases. Percent complementarity of a SSO with a region of a target nucleic acid can be determined routinely using BLAST programs (basic local alignment search tools) and Power-BLAST programs known in the art (Altschul et al., J. Mol. Biol., 1990, 215, 403-410; Zhang and Madden, Genome Res., 1997, 7, 649-656). Percent homology, sequence identity or complementarity, can be determined by, for example, the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482-489).

As used here, a protein or nucleic acid has at least a specified percentage of sequence homology with a given SEQ ID NO, if the protein or nucleic acid in question has the same amino acid residues or bases, in the same sequence, in at least the specified percentage of residues or bases of the identified SEQ ID NO. In making nucleic acids with at least a given degree of sequence homology to a specified coding sequence, one skilled in the art, with the aid of a computer, could readily generate all nucleic acid sequences that would encode a given protein sequence. In making proteins with at least a given degree of sequence homology to specified protein sequence, one skilled in the art, guided by a knowledge of the physicochemical properties of amino acids, the position of a given residue within a protein, the known effects of certain amino acids on the conformation of proteins, and with the aid of a computer, could readily select certain amino acid substitutions at certain residue positions that would, with reasonable predictability, preserve the functional properties of the protein.

In another embodiment, the present invention relates to a splice-switching oligonucleotide, which specifically binds an RNA species encoded by an AR gene and/or encoding an AR polypeptide. In another aspect, the present invention relates to a splice-switching oligonucleotide, which specifically binds an RNA species encoded by an EGFR gene and/or encoding an EGFR polypeptide. The splice-switching oligonucleotides comprises or consists of 5-100 nucleotides, such as preferably 5-25, for example 13-20, such as 14-18 nucleotides, for example 18 nucleotides. In a suitable embodiment, the splice-switching oligonucleotide comprises a sequence selected from any region of the AR gene or the complement thereof or the EGFR gene or the complement thereof which results in the reduction of the expression level of AR and/or EGFR in a cell, such as selected from any region that covered the splice site of exon 1 or CE3 of AR or exon 16 or exon 18 of EGFR or the complement thereof.

In some embodiments, the splice-switching oligonucleotides comprises, consist essentially of, consist of or is a sequence that is complementary to the region containing the splice site of exon CE3 or SEQ ID NO:1 (GATCTTTTTAAGGCTGAA=SEQ ID NO:1). In one embodiment, the splice-switching oligonucleotide comprises, consists essentially of, consists of or is the AR-V7 SSO sequence mG*mC*mC*mA*mA*mC*mC* mC*mG*mG*mA*mA*mU*mU*mU*mU*mU*mC (SEQ ID NO:3) (m_*=nucleotides are chemically modified to contain 2'-O-Me phosphorothioate backbones). In one embodiment, the splice-switching oligonucleotides comprises, consists essentially of, consists of or is the AR-45 SSO sequence mG*mG*mA*mA*mA*mA*mA* mC*mU*mU*mA*mC*mC*mG*mC*mA*mU*mG (SEQ ID NO:4) (m_*=nucleotides are chemically modified to contain 2'-O-Me phosphorothioate backbones). In one embodiment, the splice switching oligonucleotide comprises, consists essentially of, or is a sequence complementary to SEQ ID NO: 1.

In some embodiments, the splice-switching oligonucleotides comprises, consist essentially of, consist of or is a sequence that is complementary to the region containing the splice site of exon 1 (GTACGCCATTCAAAAAGG, SEQ ID NO: 2). In one embodiment, the splice switching oligonucleotide comprises, consists essentially of, or is a sequence complementary to SEQ ID NO: 2.

In some embodiments, the splice-switching oligonucleotides comprises, consists essentially of, consists of or is a sequence that is complementary to the region containing exon 16 or exon 18 of EGFR. The sequence of Exon 16 (SEQ ID NO:7) and Exon 18 (SEQ ID NO:8) can be found below. In one embodiment, the splice-switching oligonucleotides comprises, consists essentially of, consists of or is the EGRF-ex16 SSO sequence mG*mC*mU*mG*mU* mG*mA*mA*mC*mA*mC*mU*mU*mA*mC*mC*mC* mA (SEQ ID NO:5) (m_*=nucleotides are chemically modified to contain 2'-O-Me phosphorothioate backbones). In one embodiment, the splice-switching oligonucleotides comprises, consists essentially of, consists of or is the EGRF-ex18 SSO sequence mC*mC*mA*mG*mG* mG*mA*mC*mC*mU*mU*mA*mC*mC*mU*mU*mA* mU (SEQ ID NO:6) (m_*=nucleotides are chemically modified to contain 2'-O-Me phosphorothioate backbones). In one embodiment, the splice switching oligonucleotide comprises, consists essentially of, or is a sequence complementary to exon 16 or exon 18 of EGFR.

In another embodiment, the present invention employs splice switching oligonucleotides or splice switching oligomers (SSOs) to control the alternative splicing of AR or EGFR so that there is reduction of the expression of AR and/or EGFR in the cancer.

In one embodiment, an SSO (AR-V7 SSO) reduces splicing of the AR pre-mRNA to AR-V7 (the constitutively active truncated AR) and increases splicing of the wildtype AR. In a preferred embodiment, the AR-V7 SSO comprises, consists essentially of or is SEQ ID NO: 3. In a second embodiment; an SSO (AR-45 SSO) drives production of a dominant-negative AR45 variant and reduces production of the wildtype AR. In a preferred embodiment, the AR-45 SSO comprises, consists essentially of or is SEQ ID NO:4. In another embodiment, an SSO inhibits pEGFR expression by production of a dominant-negative EGFR variant. In some embodiment, the SSO is complementary to exon 16 or exon 18 of EGFR. In a preferred embodiment, the EGFR-exon 16 SSO comprises, consists essentially of or is SEQ ID NO: 5. In a preferred embodiment, the EGFR-exon 18 SSO comprises, consists essentially of or is SEQ ID NO: 6.

Accordingly, one embodiment of the present invention is a method of treating a cancer by administering SSOs to a patient. The SSOs that are administered alter the splicing of a pre-mRNA of either AR and/or EGFR to reduce expression of AR and/or EGFR in the cancer of the patient. In some embodiments, the SSOs produce a dominant negative form of either AR or EGFR.

The invention can be practiced with SSOs comprised of several chemistries that hybridize to RNA, but that do not activate the destruction of the target RNA by RNase H, as do conventional antisense 2'-deoxy oligonucleotides. These oligonucleotides may contain modified, e.g. non-naturally occurring internucleoside linkages. For example, in some embodiments, the oligonucleotides have one or more modified internucleoside linkages. The splice-switching oligonucleotides of the invention in one embodiment comprise one or more modified nucleotides, such as a locked nucleic acid (LNA) or methylated nucleotides. LNA, often referred to as inaccessible RNA, is a modified RNA nucleotide. The ribose moiety of an LNA nucleotide is modified with an extra bridge connecting the 2' oxygen and 4' carbon. The invention can be practiced using 2'O modified nucleic acid oligomers, such as where the 2'O is replaced with —O—CH3, —O—CH2-CH2-O—CH3, —O—CH2-CH2-CH2-NH2, —O—CH2-CH2-CH2-OH or —F, where 2'O-methyl (2'-OMe) or 2'O-methyloxyethyl (MOE) is preferred. The nucleobases do not need to be linked to sugars.

A number of chemical modifications increase binding affinity, stability and delivery of oligonucleotides to cells and tissues and can be used in the practice of the current invention. Oligonucleotides containing 2'-O-Me phosphorothioate backbones have been used by our collaborators to correct aberrant splicing of modified luciferase pre-mRNA (Kotula, J. W., et al., Aptamer-mediated delivery of splice-switching oligonucleotides to the nuclei of cancer cells. Nucleic Acid Ther, 2012. 22(3): p. 187-95) and by others to correct splicing of USH1C and rescue hearing and vestibular function (Lentz, J. J., et al., Rescue of hearing and vestibular function by antisense oligonucleotides in a mouse model of human deafness. Nat Med, 2013. 19(3): p. 345-50). Additional studies have shown efficacy and, in some cases, superior efficacy of oligonucleotides containing other types of chemically modified backbones. For example, correction of splicing of modified enhanced green fluorescent protein pre-mRNA by oligonucleotides containing morpholino, peptide nucleic acid, locked nucleic acid and 2'-O-(2-methoxyethyl) modified backbones (Sazani, P., et al., Nuclear antisense effects of neutral, anionic and cationic oligonucleotide analogs. Nucleic Acids Res, 2001. 29(19): p. 3965-74; Roberts, J., et al., Efficient and persistent splice switching by systemically delivered LNA oligonucleotides in mice. Mol Ther, 2006. 14(4): p. 471-5; Sazani, P., et al., Systemically delivered antisense oligomers upregulate gene expression in mouse tissues. Nat Biotechnol, 2002. 20(12): p. 1228-33; Veedu, R. N. and J. Wengel, Locked nucleic acids: promising nucleic acid analogs for therapeutic applications. Chem Biodivers, 2010. 7(3): p. 536-42, the contents of which are incorporated by reference in their entireties), decrease of STAT3 and antitumor activity in lymphoma and lung cancer as well as in patients in a Phase I dose escalation study by oligonucleotides containing 2'-O-(2-methoxyethyl) modified backbones (Hong, D., et al., AZD9150, a next-generation antisense oligonucleotide inhibitor of STAT3 with early evidence of clinical activity in lymphoma and lung cancer. Sci Transl Med, 2015. 7(314): p. 314ra185) and reduction of methyl-CpG-binding protein 2 (MeCP2) to rescue MECP2 duplication syndrome and correct MECP2 levels in cells from MECP2 duplication patients by oligonucleotides containing 2'-O-(2-methoxyethyl) modified backbones (Sztainberg, Y., et al., Reversal of phenotypes in MECP2 duplication mice using genetic rescue or antisense oligonucleotides. Nature, 2015. 528(7580): p. 123-6).

It will be obvious to one skilled in the art that additional oligomer chemistries can be used to practice the invention including phosphorodiamidate-linked morpholino oligomers (PMO) or locked nucleic acid (LNA) oligomers.

The SSOs of this invention can be made through the well-known technique of solid phase synthesis. Any other means for such synthesis known in the art can additionally or alternatively be used. It is well known to use similar techniques to prepare oligonucleotides such as the phosphorothioates and alkylated derivatives. Suitable SSOs can also be ordered from suitable oligomer companies, for example Bio Basic (biobasic.com) which can provide SSOs containing chemically modified 2'-O-Me phosphorothioate backbones.

The bases of the SSO can be the conventional cytosine, guanine, adenine and uracil or thymidine bases. Alternatively, modified bases can be used. Of particular interest are modified bases that increase binding affinity. One non-limiting example of preferred modified bases are the so-called G-clamp or 9-(aminoethoxy)phenoxazine nucleotides, cytosine analogues that form 4 hydrogen bonds with guanosine. (Flanagan, W. M., et al., 1999, Proc. Natl. Acad. Sci. 96:3513; Holmes, S. C., 2003, Nucleic Acids Res. 31:2759). Specific examples of other bases include, but are not limited to, 5-methylcytosine (MeC), isocytosine, pseudoisocytosine. 5-(1-propynyl)-cytosine, 5-bromouracil, 5-(1-propynyl)-uracil, 5-propyny-6,5-methylthiazoleuracil, 6-aminopurine, 2-aminopurine, inosine, 2,6-diaminopurine, 7-propyne-7-deazaadenine, 7-propyne-7-deazaguanine and 2-chloro-6-aminopurine.

Compositions comprising the splice-switching oligonucleotides are also provided. In some embodiments, the compositions further comprise a pharmaceutically acceptable carrier. Pharmaceutically acceptable carriers are well known to those of ordinary skill in the art (Arnon, R. (Ed.) Synthetic Vaccines I:83-92, CRC Press, Inc., Boca Raton, Fla., 1987). They include liquid media suitable for use as vehicles to introduce the splice-switching oligonucleotides into a subject.

In a preferred embodiment, the SSO's are stored in a lyophilized product until use. In other embodiments, SSOs can be resuspended in nuclease free water and stored.

Cells can be transfected with SSOs in Opti-MEM medium, and cells can be cultured in medium known in the art, for example, medium containing LNCaP, H520, A549, 22RV1: phenol red-free RPMI 1640+10% FBS; LN95: phenol red-free RPMI+10% charcoal stripped FBS; PC3, VCaP: DMEM+10% FBS; MDA PCa 2b: F12-K+20% FBS+25 ng/mL cholera toxin+10 ng/mL EGF+0.005 mM phosphoethanolamine+100 pg/mL hydrocortisone+45 nM selenious acid+0.005 mg/mL insulin, and the like.

Methods of treating a subject suffering from a disease are also contemplated. The method comprises administering to the subject a therapeutically effective amount of a splice-switching oligonucleotide described herein or a composition comprising the SSO such that the disease is treated. In preferred embodiments, the disease is cancer. In a preferred embodiment, the cancer is prostate cancer.

In some embodiments, the method of treatment further comprises administering to the subject a second cancer therapy. The combination of the SSOs and the second cancer therapy results in an increase in the efficacy of the treatment of the cancer than the second therapy administered alone.

In some embodiments, the second cancer therapy is a therapy known to one skilled in the art, including, for example a second therapy selected from the group consisting of chemotherapy, hormone therapy, androgen therapy, radiation, surgery, vaccine therapy and combinations thereof. In one embodiment, the second cancer therapy is MDV3100 (enzalutamide).

Clinical studies and associated delivery options for SSOs that can be used in the practice of the invention can be found in for example, Kole, R. and A. M. Krieg, *Exon skipping therapy for Duchenne muscular dystrophy*. Adv Drug Deliv Rev, 2015. 87: p. 104-7; Zanetta, C., et al., Molecular therapeutic strategies for spinal muscular atrophies: current and future clinical trials. Clin Ther, 2014. 36(1): p. 128-40; and Hong, D., et al., AZD9150, a next-generation antisense oligonucleotide inhibitor of STAT3 with early evidence of clinical activity in lymphoma and lung cancer. Sci Transl Med, 2015. 7(314): p. 314ra185, the contents of which are incorporated by reference in their entireties.

Methods or reducing the expression of AR and/or EGFR in a cancer cell are also provided. The method comprises treating the cancer cell with an SSO described herein. In some embodiments, the cancer cell is in a subject suffering from the cancer.

In one embodiment, the SSO of the invention inhibits the expression of AR and/or EGFR causing a reduction of RNA by at least 10%, by at least 20%, by at least 25%, by at least 30%, by at least 40%, by at least 50%, by at least 60%, by at least 70%, by at least 75%, by at least 80%, by at least 85%, by at least 90%, by at least 95%, by at least 98%, by at least 99%, or by 100% in at least one cell.

In some embodiments, the SSOs may be delivered via aptomers, Inverse Molecular Sentinel nanoprobes, SSO encapsulated liposome-DNA-polycation or SSO encapsulated liposome-protamine-hyluronic acid nanoparticles and the like. Suitable methods of delivering aptamers can be found in Kotula, J. W., et al., Aptamer-mediated delivery of splice-switching oligonucleotides to the nuclei of cancer cells. Nucleic Acid Ther, 2012. 22(3): p. 187-95, the contents of which are incorporated by reference in their entirety. SSOs can be delivered to prostate cancer cells using Inverse Molecular Sentinel nanoprobes, methods of making can be found in Vo-Dinh, T., et al., *SERS nanosensors and nanoreporters: golden opportunities in biomedical applications*. Wiley Interdiscip Rev Nanomed Nanobiotechnol, 2015. 7(1): p. 17-33, which are incorporated by reference in their entirety.

Compositions of the present invention may comprise sterile aqueous and nonaqueous injection solutions of the SSOs, which preparations are preferably isotonic with the blood of the intended subject and essentially pyrogen free. These preparations may contain anti-oxidants, buffers, bacteriostats, and solutes which render the formulation isotonic with the blood of the intended subject. Aqueous and non-aqueous sterile suspensions can include, but are not limited to, suspending agents and thickening agents. The formulations may be presented in unit dose or multi-dose containers, for example, sealed ampoules and vials, and may be stored in freeze-dried (lyophilized) condition requiring only the addition of the sterile liquid carrier, for example, saline or water-for-injection immediately prior to use.

In some embodiments, the compositions of the SSOs may be contained within a lipid particle or vesicle, such as a liposome or microcrystal, which may be suitable for parenteral administration. The particles may be of any suitable structure, such as unilamellar or plurilameller, so long as the SSOs are contained therein. Positively charged lipids such as N-[1-(2,3-dioleoyloxi)propyl]-N,N,N-trimethyl-ammonium-methylsulfate, or "DOTAP," are particularly preferred for such particles and vesicles. The preparation of such lipid particles is well known. [See references in U.S. Pat. No. 5,976,879 col. 6, incorporated by reference in its entirety]. Methods of delivery of SSOs using nanoparticles can be found in Huang et al. and Chono et al. and have been successfully utilized by Bauman et al. to deliver the SSO redirecting splicing of the Bcl-x pre-mRNA to a murine melanoma tumor model (See, e.g. Bauman, J. A., et al., *Anti-tumor activity of splice-switching oligonucleotides.* Nucleic Acids Res, 2010. 38(22): p. 8348-56; Li, S. D., S. Chono, and L. Huang, Efficient oncogene silencing and metastasis inhibition via systemic delivery of siRNA. Mol Ther, 2008. 16(5): p. 942-6; and Li, S. D., S. Chono, and L. Huang, Efficient gene silencing in metastatic tumor by siRNA formulated in surface-modified nanoparticles. J Control Release, 2008. 126(1): p. 77-84, Chono, S., et al., An efficient and low immunostimulatory nanoparticle formulation for systemic siRNA delivery to the tumor. J Control Release, 2008. 131(1): p. 64-9, which are incorporated by reference in their entireties). Methods whereby bodily fluids, organs or tissues are contacted with an effective amount of one or more of the splice-switching oligonucleotides or compositions of the invention are also contemplated. Bodily fluids, organs or tissues can be contacted with one or more of the splice-switching oligonucleotides of the invention resulting in modulation of AR and/or EGFR expression in the cells of bodily fluids, organs or tissues. An effective amount can be determined by monitoring the modulatory effect of the splice-switching oligonucleotides or compositions on target nucleic acids or their products by methods routine to the skilled artisan.

The present invention provides for the use of SSOs described above for the preparation of a medicament for controlling the alternative splicing of androgen receptor (AR) and/or EGFR, specifically for reducing the expression of AR and/or EGFR in tumor cells. In the manufacture of a medicament according to the invention, the SSOs are typically admixed with, inter alia, an acceptable carrier. The carrier must be acceptable in the sense of being compatible with any other ingredients in the composition and must not be deleterious to the patient. The carrier may be a solid or liquid.

Aspects of the present disclosure that are described with respect to methods can be utilized in the context of the pharmaceutical compositions or kits discussed in this disclosure. Similarly, aspects of the present disclosure that are described with respect to the pharmaceutical compositions can be utilized in the context of the methods and kits, and aspects of the present disclosure that are described with respect to kits can be utilized in the context of the methods and compositions.

This disclosure provides kits. The kits can be suitable for use in the methods described herein. Suitable kits include a kit for treating a disease or condition, specifically cancer comprising a composition comprising at least one splice-switching oligonucleotide described herein. In one aspect, the kit provides pharmaceutical composition comprising SSOs in amounts effective for treating cancer, more preferably prostate cancer. In some aspects, the kits provides a composition comprising at least one SSO and at least one second cancer therapy. In some aspects, instructions on how to administer the composition and/or SSOs.

The following non-limiting examples are included for purposes of illustration only, and are not intended to limit the scope of the range of techniques and protocols in which the compositions and methods of the present invention may find utility, as will be appreciated by one of skill in the art and can be readily implemented.

EXAMPLES

Example 1: SSOs to Alter Splice Variants of AR and EGFR

Herein we have designed and synthesized novel SSOs targeting AR and EGFR pre-mRNAs to produce inhibitory splice variants and correct aberrant splicing as follows. We have synthesized a SSO to correct the aberrant splicing that leads to production of the constitutively active AR-V7 variant. Transfection of prostate cancer cells with this chemically modified SSO, which targets the splice site of the cryptic exon included in AR-V7, decreases AR-V7 RNA and protein, colony formation and proliferation of cells. In addition, we have synthesized a SSO to drive production of a naturally occurring dominant-negative AR variant (AR45) leading to interference with wild type AR transactivation activity. Transfection of prostate cancer cells with this chemically modified SSO, which targets the splice site of the first exon of wild type AR and leads to inclusion of an alternative first exon encoding the unique N-terminal extension characterizing AR45, increases AR45 RNA, decreases AR and AR-V7 and modulates AR signaling. Furthermore, we have synthesized SSOs targeting exons in the transmembrane domain and the tyrosine kinase domain of EGFR to drive production of a soluble, naturally expressed inhibitory EGFR isoform and a dominant-negative EGFR isoform, respectively. Transfection of prostate cancer cells with these chemically modified SSOs increase RNA corresponding to these isoforms and inhibit pEGFR protein expression.

These studies suggest that SSOs can be developed to modulate AR and EGFR signaling. Such SSOs are novel therapeutic modalities to combat prostate cancer in AA men as well as men of all races with aggressive disease driven by these mechanisms.

Example 2: Aberrant AR Splicing

An agent to correct aberrant AR splicing leading to production of constitutively active AR splice variants Background: AR variants resulting from splicing of alternative or "cryptic" exons to the exons encoding the AR N-terminal domain or DNA-binding domain have been identified in prostate cancer cell lines, xenograft tumors, and clinical specimens (4, 32-36). Moreover, androgen-independent cell lines, castration resistant xenograft tumors, and CRPC patient samples exhibit higher levels of such alternatively spliced products, and higher levels of such AR variants have been shown to correlate with poorer clinical outcomes. Furthermore, increases in these alternatively spliced products have been seen in prostate cancer cell lines treated with MDV3100 (37). Consistent with the structures of these variants, it has been shown that these AR variants are constitutively active. Thus, an agent correcting aberrant AR splicing has the potential to abrogate retained AR signaling and when used in combination with MDV3100 enhance cytotoxicity.

Hypothesis: Production of constitutively active AR splice variants is a mechanism prostate cancer cells utilize to survive in the MDV3100 environment, and an agent correcting aberrant AR splicing in combination with MDV3100 will enhance cytotoxicity.

Experimental Strategy: Levels of AR-V7, a constitutively active AR splice variant that has been detected in CRPC specimens and a prostate cancer cell line treated with MDV3100, will be detected by quantitative RT-PCR in 22Rv1 and LNCaP cells prior to treatment with MDV3100, during treatment with MDV3100, and at regrowth post treatment with MDV3100 and in xenografts derived from the pre- and post-MDV3100 cell lines. It should be noted that other/additional cell lines may be used depending on our initial observations and results. An agent to correct the aberrant splicing leading to the production of AR-V7 was developed. Splice-switching oligonucleotides (SSOs) modulate pre-mRNA splicing by binding to target pre-mRNAs and blocking access of the splicing machinery to a particular splice site (38). Thus, SSOs can be used to produce novel splice variants, correct aberrant splicing or manipulate alternative splicing. We will synthesize a chemically modified SSO that corrects aberrant AR pre-mRNA splicing leading to the production of AR-V7 as depicted in FIG. 1. Aberrant usage of the splice site of exon CE3 leads to its inclusion and premature termination of AR, resulting in production of AR-V7. Specifically, we synthesized an oligonucleotide (AR-V7 SSO, mG*mC*mC*mA*mA*mC*mC*mC*mG*mG*mA*mA*mU*mU*mU*mU*mU*mC, SEQ ID NO: 3) consisting of sequence that is complementary to the region containing the splice site of exon CE3 (GATCTTTTTAAGGCTGAA, SEQ ID NO: 1), reducing production of AR-V7. In addition, we will synthesize 4 more oligonucleotides consisting of sequences that encompass various iterations of the aforementioned sequence plus 4 nucleotides upstream and downstream of this sequence to ensure the generation of a SSO that is most effective in blocking the splice site of exon CE3. The pre- and post-MDV3100 cell lines are transfected with the SSO and assays for transcriptional activity of transiently transfected reporter genes, endogenous AR target gene transcription, transcript levels, and growth of transfected cells in the presence and absence of synthetic androgen are done. The SSO are appended to an aptamer. Single-stranded DNA or RNA aptamers that target cell surface proteins such as PSMA have shown promise as delivery agents, able to increase the efficiency by which cells expressing these proteins internalize therapeutic oligonucleotides linked to these aptamers (39-45). For example, we have previously demonstrated the ability of a PSMA aptamer to deliver a siRNA targeting the expression of PLK1 to the cytoplasm of prostate cancer cells expressing PSMA, resulting in PLK1 knockdown, decreased proliferation, increased apoptosis and tumor regression (39). One limitation of this approach is that it is unable to target key nuclear events. During the past few years it has become apparent that certain proteins shuttle between the cell surface and the nucleus. The most extensively studied of these proteins is nucleolin, a helicase involved in ribosome biogenesis that bas also been shown to function as a cell surface receptor (46). We and others have shown that a DNA aptamer that binds nucleolin is readily taken up into cancer cells which express high levels of nucleolin on their surface and migrates to the nucleus (47). In addition, we have shown that a nucleolin aptamer can selectively and effectively deliver SSOs to the nucleus of prostate cancer cells and restore proper splicing of a luciferase reporter construct (48). The SSO correcting the aberrant splicing leading to the production of AR-V7 will be appended to the nucleolin aptamer. The aforementioned assays are repeated in the pre- and post-MDV3100 cells treated with the aptamer-therapeutic oligonucleotide chimera. Xenografts derived from the pro- and post-MDV3100 cell lines are treated with the chimera and assays for tumor growth, toxicity, and histology. Again, other/additional cell lines may be used.

Figure 4A:
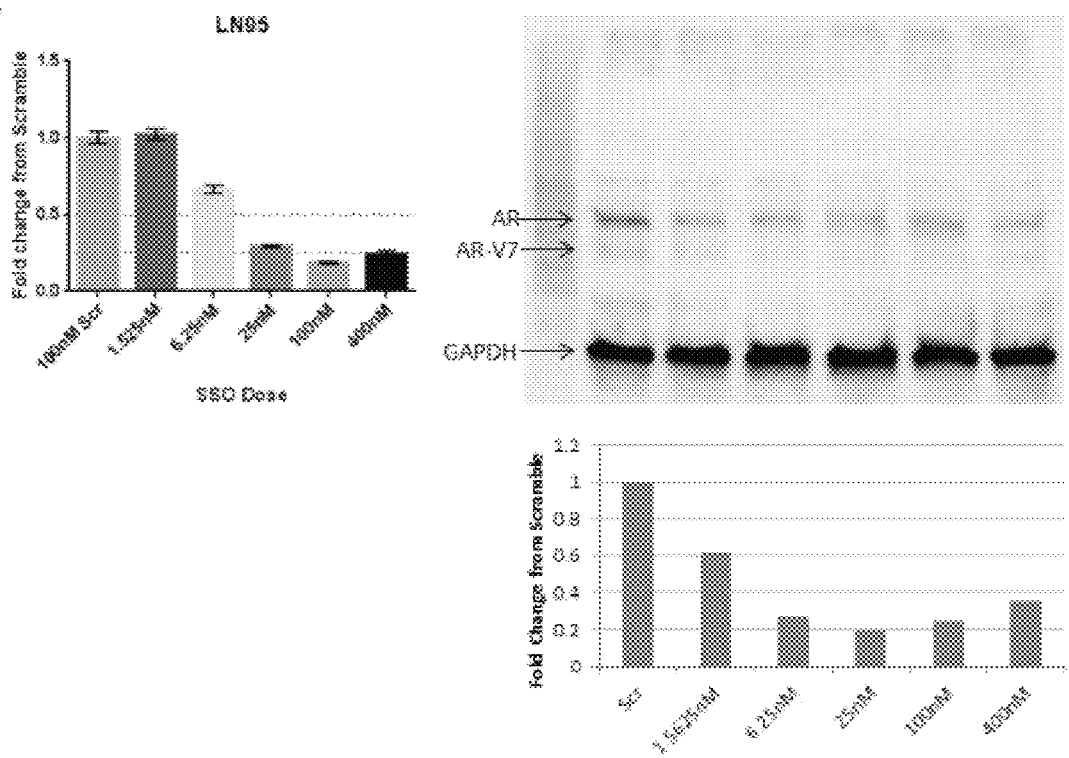
FIG. 4A depicts AR-V7 SSO inhibiting AR-V7 RNA (left) and protein (right) in a dose-dependent manner in LN95 prostate cancer cells derived from a white prostate cancer patient.
Figure 4D:
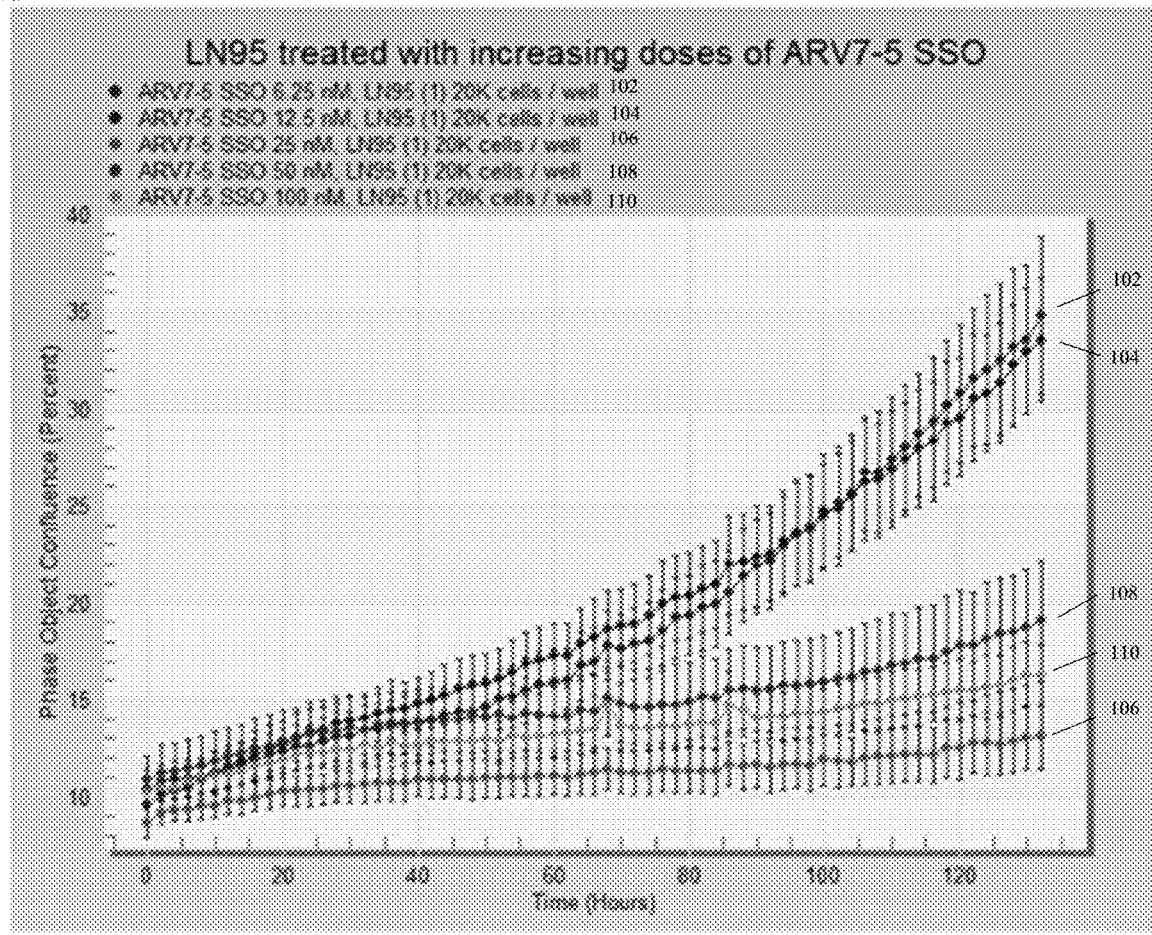
FIG. 4D is a graph depicting AR-V7 SSO inhibiting proliferation of LN95 prostate cancer cells.
Figure 4E:
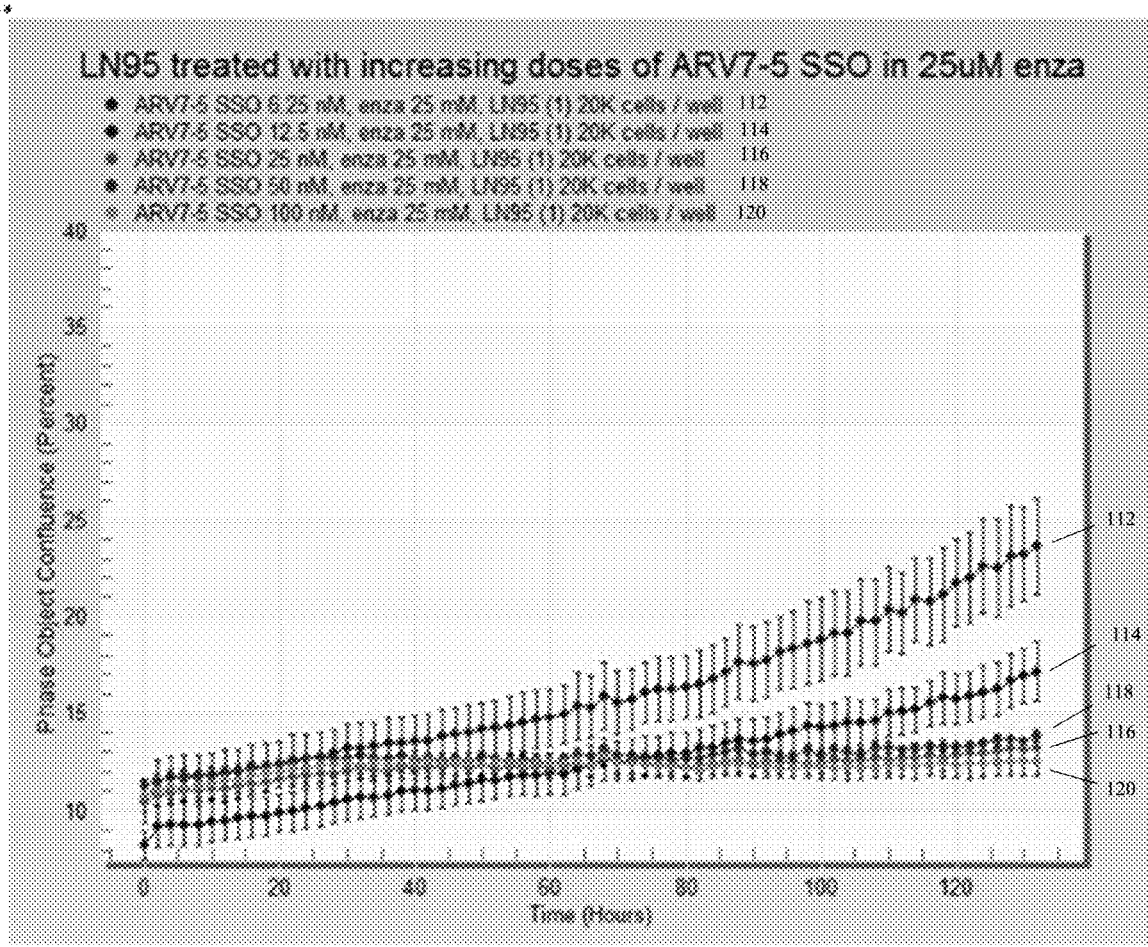
FIGS. 4E and 4F are graphs depicting AR-V7 SSO inhibiting proliferation of LN95 prostate cancer cells in the presence of enzalutmide. SSO=splice switching oligonucleotide, Scr=control scrambled SSO, AR=androgen receptor.
Figure 4F:
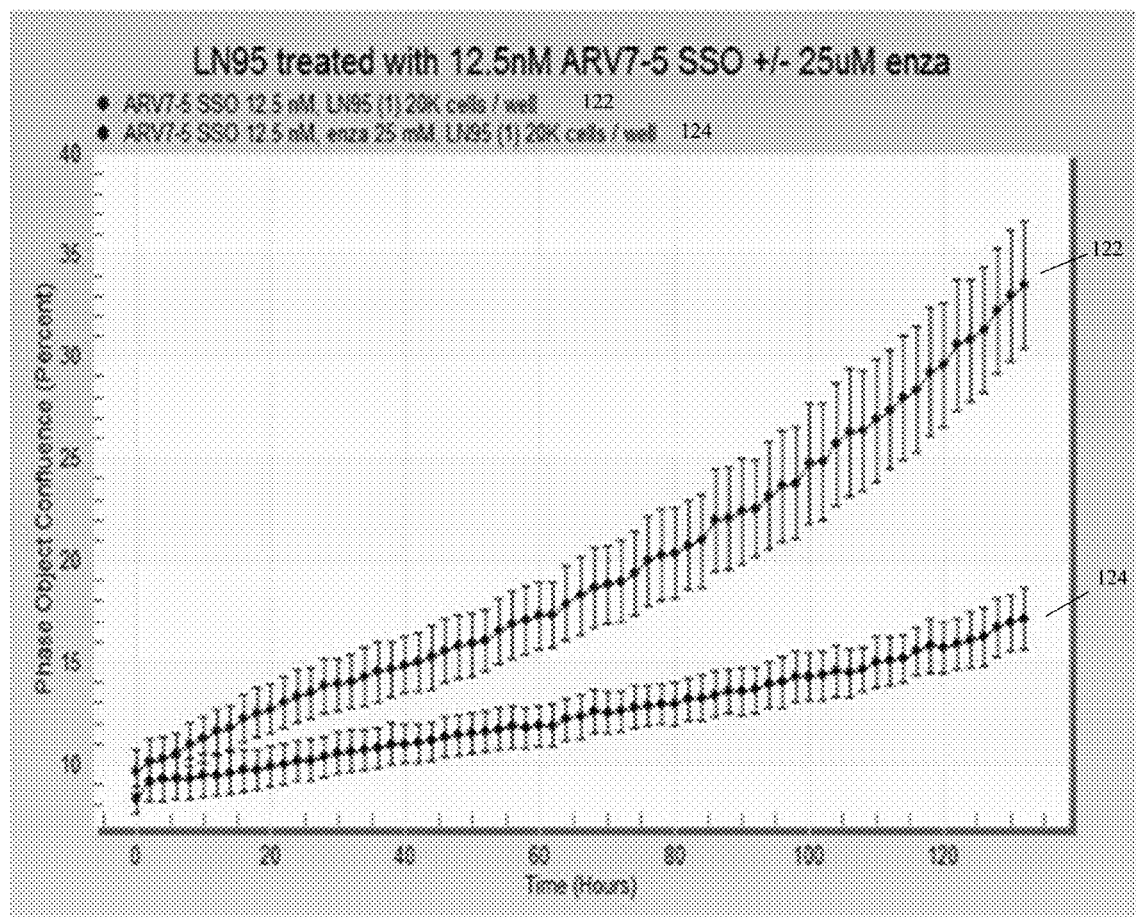
Figure 5:
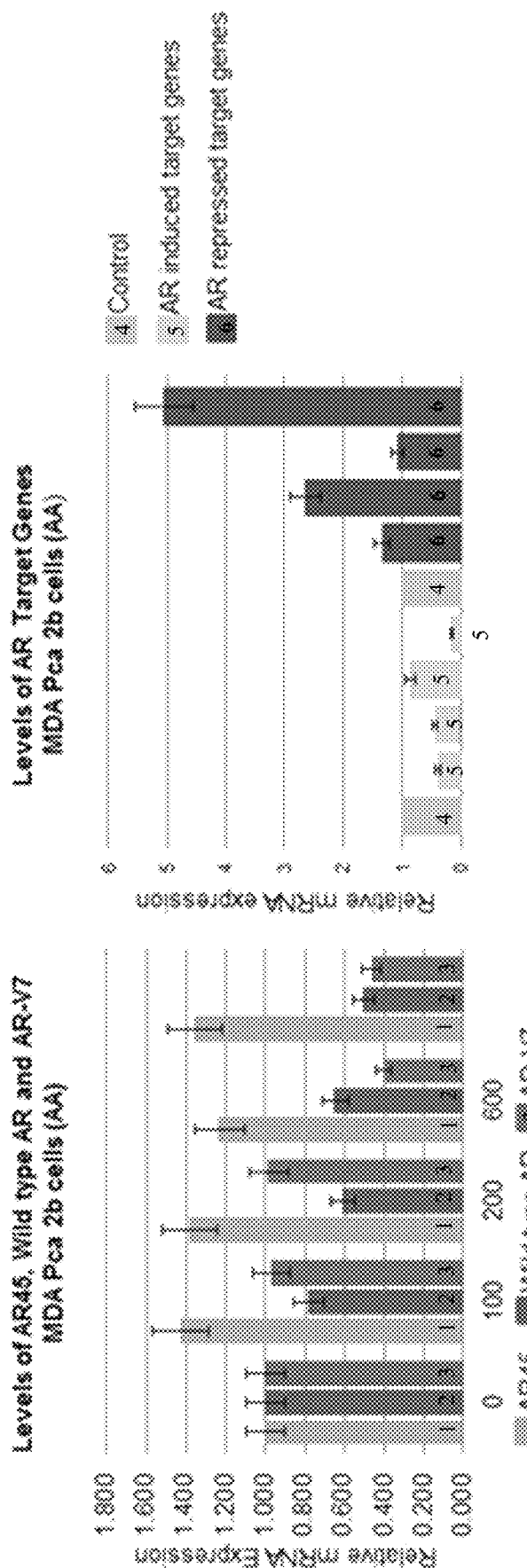
FIG. 5 are graphs showing that AR45 SSO drives production of AR45, simultaneously decreasing wild type AR and AR-V7 (left) and modulating AR signaling (right) in MDA PCa 2b prostate cancer cells derived from an African American patient. SSO=splice switching oligonucleotide, AR=androgen receptor, AA=African American.

Dose-dependent inhibition of AR-V7 by this SSO targeting the CE3 exon corrects aberrant splicing and leads to a reduction in the production of the constitutively active AR variant AR-V7 as demonstrated in FIGS. 4A and 4B. LN95, VCaP, 22Rv1 and MDA PCa 2b cells were treated with control scrambled SSO or with increasing concentrations of AR-V7 SSO, as indicated. RNA was harvested 72 hours after transfection for cDNA production and QRT-PCR analysis. Ct values were normalized to TBP, TATA-binding protein, in each sample and used to generate relative expression values.

Example 3: An Agent to Drive Production of a Dominant-Negative AR Variant

Background: Much evidence suggests that the N-terminal domain of the AR is absolutely required for its androgen-dependent and androgen-independent transactivation activity (49). A naturally occurring variant of the AR, AR45, consists of a unique N-terminal extension connected to an intact DNA-binding domain, binge, and ligand-binding domain (50). Consistent with its structure, ligand is able to bind to AR45 and AR45 is able to localize to the nucleus, but it has no transactivation activity in the presence or absence of synthetic androgen. Moreover, AR45 acts in a dominant-negative manner to interfere with wild type AR transactivation activity. Accordingly, AR45 inhibits proliferation of prostate cancer cells. Thus, an agent driving production of AR45 has the potential to abrogate retained AR signaling and when used in combination with MDV3100 enhance cytotoxicity.

Hypothesis: An agent driving production of a dominant-negative AR variant in combination with MDV3100 will enhance cytotoxicity.

Figure 6:
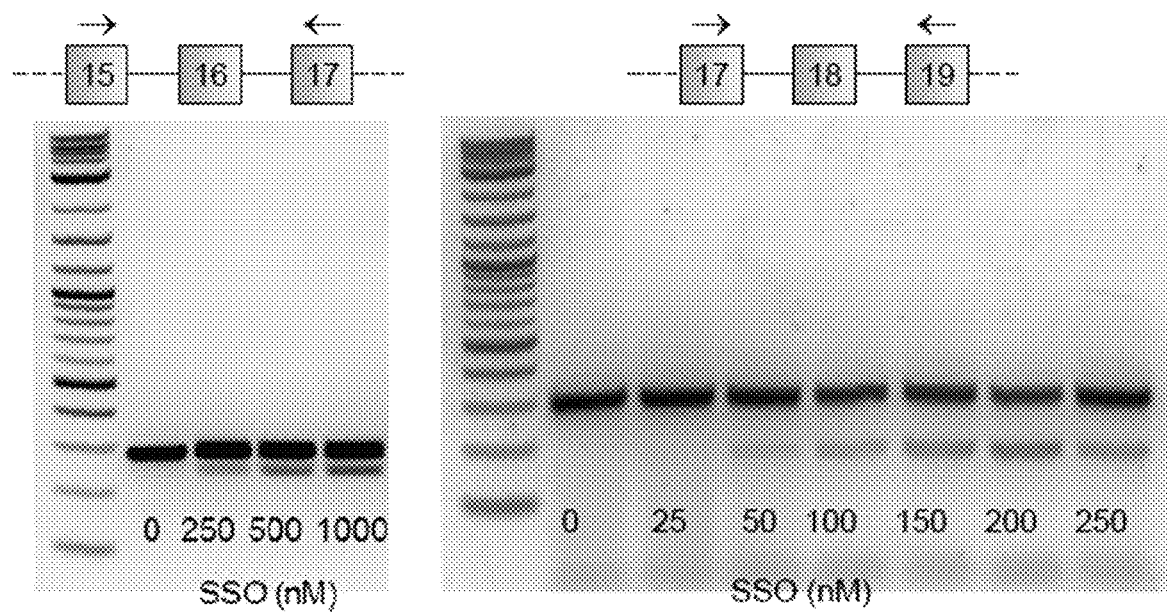
FIG. 6 contains gel images demonstrating that SSOs drive production of dominant-negative EGFR variants in a dose-dependent manner. LNCaP cells were treated with transfection reagent alone or with increasing concentrations of exon 16 (left) or exon 18 (right) SSO. RNA was harvested 72 hrs after transfection. Targets were visualized by RT-PCR using primers located in the exons flanking the target exon, as depicted above the gel images. Products were confirmed by sequencing.
Figure 7:
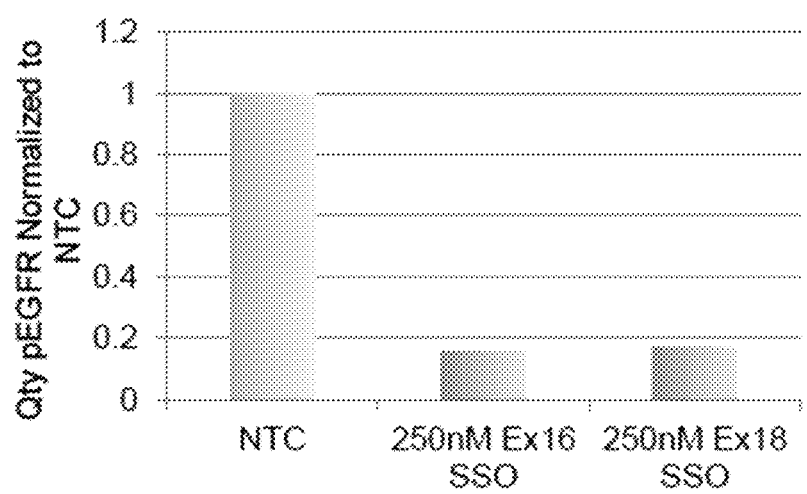
FIG. 7 is a graph depicting inhibition of pEGFR expression by SSOs driving production of dominant-negative EGFR variants. LNCaP cells were treated with transfection reagent alone or with 250 nM EGRF exon 16 or 18 SSOs. 72 hrs post transfection, cells were exposed to 10 ng/ml EGF for 10 minutes before lysing and haresting total protein. pEGFR and GAPDH were visualized via Western blot and imaged and quantified on a Licor Odyssey Fc. pEGFR quantities are normalized to GAPDH and then to vehicle control.

Experimental Strategy: We will synthesize a chemically modified SSO that drives production of AR45. Specifically, an oligonucleotide (AR45 SSO, mG*mG*mA*mA*mA*mA*mA*mC*mU*mU*mA*mC*mC*mG*mC*mA*mU*mG, SEQ ID NO: 4) consisting of sequence that is complementary to the region containing the 5' splice site of exon 1 (GTACGCCATTCAAAAAGG, SEQ ID NO: 2) is produced. As shown in FIG. 2, this leads to the inclusion of exon 1B and thus production of AR45. In addition, we are synthesizing 4 additional oligonucleotides consisting of sequences that span various regions of the aforementioned sequence plus 4 nucleotides upstream and downstream of this sequence to generate a SSO that blocks the 5' splice site of exon 1 most efficiently. We delivered the SSO and tested its potency as described in Example 2 above.

As demonstrated in FIG. 6 (left), AR45 SSO drives production of the dominant-negative AR variant, AR45, while simultaneously decreasing expression of full-length AR and the constitutively active AR variant, AR-V7. MDA PCa 2b cells were treated with transfection reagent alone or with increasing concentrations of AR45 SSO, as indicated. RNA was harvested 72 hours after transfection for cDNA production and QRT-PCR analysis. Ct values were normalized to TBP, TATA-binding protein, in each sample and used to generate relative expression values.

Modulation of AR signaling by SSO driving production of the dominant-negative AR variant AR45 as shown in FIG. 6 (right). MDA Pca 2b cells were treated with transfection reagent alone or with 400 nM AR45 SSO. RNA was harvested 72 hours after transfection for cDNA production and QRT-PCR analysis (Light green=known AR induced targets, dark green=known AR repressed targets).

Example 4: SSOs that Target EGFR Splicing

Figure 3:
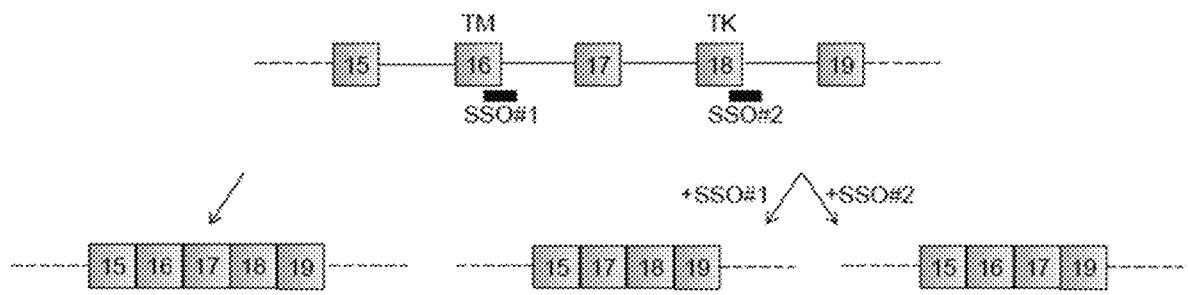
FIG. 3 is a cartoon depiction of the splicing of EGFR. Normal splicing of EGFR pre-mRNA leads to production of wild type EGFR (left). SSOs can drive production of dominant-negative EGFR variants (middle and right). A SSO blocks the splice site of exon 16 leading to skipping of exon 16 and thus production of a dominant negative EGFR variant (middle). A SSO that blocks the splice site of exon 18 leading to skipping of exon 18 and thus production of a dominant negative EGFR variant (right). TM=transmembrane domain, TK=tyrosine kinase domain.

SSOs that target the exons encoding the transmembrane and tyrosine kinase domains within the EGFR pre-mRNA are synthesized to drive production of a soluble, naturally expressed inhibitory EGFR isoform and a dominant-negative EGFR isoform, respectively. FIG. 3 shows the schematic of the alternatively spliced isoforms of EGFR. A first SSO (SSO #1) blocks the splice site of exon 16 leading to the skipping of exon 16 and thus production of a dominant negative EGFR variant. A second SSO (SSO #2) blocks the splice site of exon 18, leading to skipping of exon 18 and thus production of a dominant negative EGFR variant.

Figure 8:
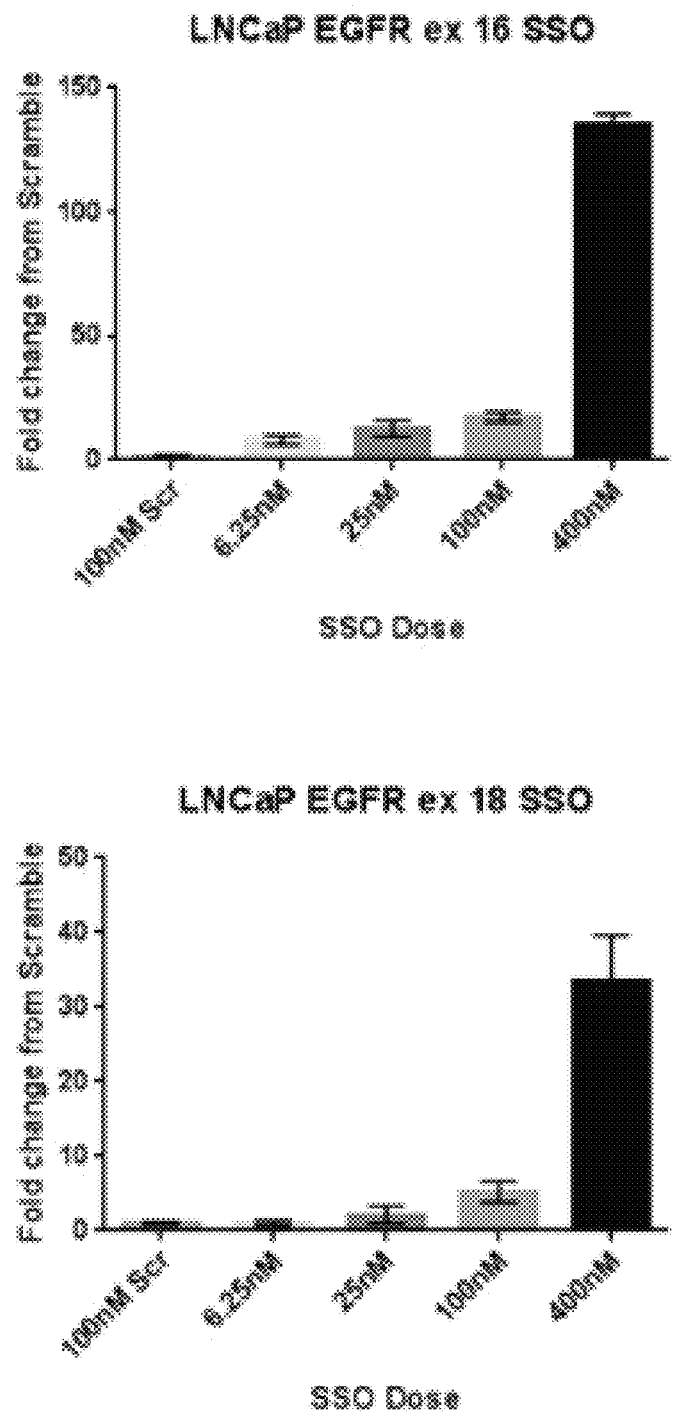
FIG. 8 are graphs quantitating the ability of EGFR-TM (exon 16) and -TK (exon 18) SSOs to drive production of dominant-negative EGFR variants in a dose-dependent manner.

As demonstrated in FIG. 8, SSOs drive production of dominant-negative EGFR variants in a dose-dependent manner. LNCaP cells were treated with transfection reagent alone or with increasing concentrations of exon 16 (SSO #1, left in FIG. 8) or exon 18 (SSO #2, right in FIG. 8). RNA was harvested 72 hours after transfection. Targets were visualized by RT-PCR using primers located in the exons flanking the target exon, as depicted above the gel images in FIG. 8. Products were confirmed by sequencing. The primers used were:

```
EGFR exon 16 skipped product qPCR primers
F:
                                       (SEQ ID NO: 9)
TGCACCTACGGGCCTAAGA

R:
                                       (SEQ ID NO: 10)
CCTTCGCATGAAGAGGCCGA

EGFR exon 18 skipped product qPCR primers
F:
                                       (SEQ ID NO: 11)
CAGGAGAGGGAGGGACTCTG

R:
                                       (SEQ ID NO: 12)
ATCGAGGATTTCCTTGTTGGCT

EGFR exon 16 endpoint PCR primers
F:
                                       (SEQ ID NO: 13)
ACGGGGACCAGACAACTGTA

R:
                                       (SEQ ID NO: 14)
ATGAAGAGGCCGATCCCCAG

EGFR exon 18 endpoint PCR primers
F:
                                       (SEQ ID NO: 15)
GATCGGCCTCTTCATGCGA R:
                                       (SEQ ID NO: 16)
GGCCATCACGTAGGCTTCAT
``` qPCR primers correspond to those used in FIG. 10 and endpoint PCR primers correspond to those used in FIG. 8.

Inhibition of pEGFR protein expression by SSOs driving production of dominant-negative EGFR variants as shown in FIG. 9. LNCaP cells were treated with transfection reagent alone or with 250 nM EGFR exon 16 or 18 SSOs. 72 hours post transfection, cells were exposed to 10 ng/mL EGF for 10 minutes before lysing and harvesting total protein. pEGFR and GAPDH were visualized via Odyssey Fc. pEGFR quantities are normalized to GAPDH and then to vehicle control. As shown in FIG. 9, both SSOs block pEGFR protein expression.

Transfection of prostate cancer cells with the SSO to correct the aberrant splicing that leads to production of the constitutively active AR-V7 variant, decreases expression of AR-V7 RNA and protein, colony formation and proliferation in a dose-dependent manner. Further, SSO Following transfection of prostate cancer cells with the SSO to drive production of the naturally occurring dominant-negative AR45 variant, an increase in expression of AR45 RNA is seen. Simultaneously, decreases in expression of wild type AR RNA as well as AR-V7 RNA are seen. Moreover, modulation of AR signaling is detected, with decreases of RNAs corresponding to a subset of AR-induced target genes and increases of RNAs corresponding to a subset of AR-repressed target genes detected. Transfection of prostate cancer cells with SSOs to drive production of a soluble, naturally expressed inhibitory EGFR isoform and a dominant-negative EGFR isoform, increase expression of RNA corresponding to these isoforms in a dose-dependent manner. Furthermore, modulation of EGFR signaling is detected, with inhibition of pEGFR protein expression detected. Studies are underway to further examine the effects of these SSOs on AR and EGFR signaling, respectively, and the effects of these SSOs on prostate tumor cell biology.

These studies suggest that SSOs can be developed to modulate AR and EGFR signaling. Such SSOs have the potential to further our understanding of the contribution of these targeted molecular mechanisms to aggressive prostate cancer and have the potential to yield novel therapeutic modalities to combat aggressive disease driven by these mechanisms.

Sequence Listing Statement

The application includes the sequence listing that is concurrently filed in computer readable form. This sequence listing is incorporated by reference herein.

AR gene: found at www.ncbi.nlm.nih.gov/gene?Db=gene&Cmd=DetailsSearch&Term=367

```
AR exonCE3-
                                        SEQ ID NO: 1
GATCTTTTTAAGGCTGAA, AR exon 1
(GTACGCCATTCAAAAAGG, SEQ ID NO: 2)

AR-V7 SSO
                                       (SEQ ID NO: 3)
mG*mC*mC*mA*mA*mC*mC*mC*mG*mG*mA*mA*mU*mU*mU*mU*
mU*mC

AR-45 SSO
                                       (SEQ ID NO: 4)
mG*mG*mA*mA*mA*mA*mA*mC*mU*mU*mA*mC*mC*mG*mC*mA*
mU*mG

EGRF Exon 16:
                                       (SEQ ID NO: 7)
atttctctttcacttcctacagATGCACTGGGCCAGGTCTTGAAGGCTG TCCAACGAATGGgtaagtgttcacagctctgtgtcacatggacctcgtc
```

-continued aa (exon capitalized, introns lower case, SSOs bold)

EGFR Exon 18:

(SEQ ID NO: 8)

ttgtctctgtgttcttgtcccccccagCTTGTGGAGCCTCTTACACCCA

GTGGAGAAGCTCCCAACCAAGCTCTCTTGAGGATCTTGAAGGAAACTGA

ATTCAAAAGATCAAAGTGCTGGGCTCCGGTGCGTTCGGCACGGTGTAT

-continued

AAGgtaaggtccctggcacaggcctctgggctgggccgc (exon capitalized, introns lower case, SSOs bold)

EGFR-ex16 SSO (SEQ ID NO: 5)

mG*mC*mU*mG*mU*mG*mA*mA*mC*mA*mC*mU*mU*mA*mC*mC*mC*mA

EGFR-ex18 SSO (SEQ ID NO: 6)

mC*mC*mA*mG*mG*mG*mA*mC*mC*mU*mU*mA*mC*mC*mU*mU*mA*mU

---

The invention claimed is:

1. A modified splice-switching oligonucleotide (SSO), said SSO comprising:
(i) a nucleotide sequence set forth in SEQ ID NO: 6,
(ii) a length of at least 18 nucleotides and no more than 100 nucleotides,
(iii) full complementarity to a sequence within exon 18 (SEQ ID NO: 8) of an EGFR pre-mRNA, and
(iv) a modification selected from the group consisting of a 2'-O-methyl phosphorothioate, a morpholino, a phosphorodiamidate-linked morpholino (PMO), a locked nucleic acid (LNA), a peptide nucleic acid, a 2'-O-(2-methoxy ethyl) nucleotide, a G-clamp or 9-(aminoethoxy)phenoxazine nucleotide, and cytosine analogues that form 4 hydrogen bonds with guanosine.

2. The modified splice-switching oligonucleotide of claim 1, wherein the oligonucleotide consisting of 18-26 nucleotides.

3. A modified splice-switching oligonucleotide of claim 1, wherein the modified splice-switching oligonucleotide comprises a 2'-O-Me phosphorothioate backbone.

4. A composition comprising the splice-switching oligonucleotide of claim 1 and a pharmaceutically acceptable carrier.

5. A composition comprising the splice-switching oligonucleotide of claim 3 and a pharmaceutically acceptable carrier.

6. A modified splice-switching oligonucleotide of claim 1, which is a morpholino oligonucleotide.

7. A composition comprising the splice-switching oligonucleotide of claim 6 and a pharmaceutically acceptable carrier.

8. The modified splice-switching oligonucleotide of claim 1, wherein the modified splice-switching oligonucleotide comprises a 2'-O-(2-methoxyethyl) backbone.

9. A composition comprising the splice-switching oligonucleotide of claim 8 and a pharmaceutically acceptable carrier.

10. The modified splice-switching oligonucleotide of claim 1, wherein the SSO has a length of at least 18 nucleotides and no more than 50 nucleotides.

11. The modified splice-switching oligonucleotide of claim 1, wherein the SSO has a length of at least 18 nucleotides and no more than 40 nucleotides.

12. The modified splice-switching oligonucleotide of claim 1, wherein the SSO has a length of at least 18 nucleotides and no more than 30 nucleotides.

13. The modified splice-switching oligonucleotide of claim 1, wherein the SSO has a length of 18 nucleotides and comprises a phosphorodiamidate-linked morpholino (PMO) modification.

14. The modified splice-switching oligonucleotide of claim 1, wherein the SSO has a length of 30 nucleotides and comprises a phosphorodiamidate-linked morpholino (PMO) modification.

15. The modified splice-switching oligonucleotide of claim 10, wherein the SSO comprises a phosphorodiamidate-linked morpholino (PMO) modification.

16. The modified splice-switching oligonucleotide of claim 11, wherein the SSO comprises a phosphorodiamidate-linked morpholino (PMO) modification.

17. The modified splice-switching oligonucleotide of claim 12, wherein the SSO comprises a phosphorodiamidate-linked morpholino (PMO) modification.

18. A method of treating cancer in a subject, comprising administering to the subject a modified splice-switching oligonucleotide according to claim 1 in an amount effective to treat the cancer, thereby treating the cancer.

19. The method according to claim 18, wherein the cancer comprises prostate cancer.

20. The method of claim 18, wherein the subject is an African American male suffering from prostate cancer.

21. The method of claim 18, wherein the method further comprises administering to the subject a second cancer therapy.

22. The method of claim 18, wherein the modified splice-switching oligonucleotide comprising a 2'-O-Me phosphorothioate backbone.

23. A method of treating cancer in a subject, comprising administering to the subject a composition according to claim 4 in an amount effective to treat the cancer, thereby treating the cancer.

24. The method of claim 23, wherein the cancer comprises prostate cancer.

25. The method of claim 23, wherein the subject is an African American male suffering from prostate cancer.

26. The method of claim 23, wherein the modified splice-switching oligonucleotide comprising a 2'-O-Me phosphorothioate backbone.

27. A method of treating cancer in a subject, comprising administering to the subject a modified splice-switching oligonucleotide according to claim 10 in an amount effective to treat the cancer, thereby treating the cancer.

28. A method of treating cancer in a subject, comprising administering to the subject a modified splice-switching oligonucleotide according to claim 11 in an amount effective to treat the cancer, thereby treating the cancer.

29. A method of treating cancer in a subject, comprising administering to the subject a modified splice-switching oligonucleotide according to claim 12 in an amount effective to treat the cancer, thereby treating the cancer.

* * * * *

SEQUENCE LISTING

<160> NUMBER OF SEQ ID NOS: 16

<210> SEQ ID NO 1
<211> LENGTH: 18
<212> TYPE: DNA
<213> ORGANISM: Homo sapiens

<400> SEQUENCE: 1
gatcttttta aggctgaa                                                           18

<210> SEQ ID NO 2
<211> LENGTH: 18
<212> TYPE: DNA
<213> ORGANISM: Homo sapiens

<400> SEQUENCE: 2
gtacgccatt caaaaagg                                                           18

<210> SEQ ID NO 3
<211> LENGTH: 18
<212> TYPE: RNA
<213> ORGANISM: Artificial Sequence
<220> FEATURE:
<223> OTHER INFORMATION: synthetic
<220> FEATURE:
<221> NAME/KEY: modified_base
<222> LOCATION: (1)..(18)
<223> OTHER INFORMATION: 2_O_Me phosphorothioate

<400> SEQUENCE: 3
gccaacccgg aauuuuuc                                                           18

<210> SEQ ID NO 4
<211> LENGTH: 18
<212> TYPE: RNA
<213> ORGANISM: Artificial Sequence
<220> FEATURE:
<223> OTHER INFORMATION: synthetic
<220> FEATURE:
<221> NAME/KEY: modified_base
<222> LOCATION: (1)..(18)
<223> OTHER INFORMATION: 2_O_Me phosphorothioate

<400> SEQUENCE: 4
ggaaaaacuu accgcaug                                                           18

<210> SEQ ID NO 5
<211> LENGTH: 18
<212> TYPE: RNA
<213> ORGANISM: Artificial Sequence
<220> FEATURE:
<223> OTHER INFORMATION: synthetic
<220> FEATURE:

```
<221> NAME/KEY: modified_base
<222> LOCATION: (1)..(18)
<223> OTHER INFORMATION: 2_O_Me phosphorothioate

<400> SEQUENCE: 5
gcugugaaca cuuaccca                                                  18

<210> SEQ ID NO 6
<211> LENGTH: 18
<212> TYPE: RNA
<213> ORGANISM: Artificial Sequence
<220> FEATURE:
<223> OTHER INFORMATION: synthetic
<220> FEATURE:
<221> NAME/KEY: modified_base
<222> LOCATION: (1)..(18)
<223> OTHER INFORMATION: 2_O_Me phosphorothioate

<400> SEQUENCE: 6
ccagggaccu uaccuuau                                                  18

<210> SEQ ID NO 7
<211> LENGTH: 100
<212> TYPE: DNA
<213> ORGANISM: Homo sapiens

<400> SEQUENCE: 7
atttctcttt cacttcctac agatgcactg ggccaggtct tgaaggctgt ccaacgaatg     60
ggtaagtgtt cacagctctg tgtcacatgg acctcgtcaa                         100

<210> SEQ ID NO 8
<211> LENGTH: 186
<212> TYPE: DNA
<213> ORGANISM: Homo sapiens

<400> SEQUENCE: 8
ttgtctctgt gttcttgtcc ccccagctt gtggagcctc ttacacccag tggagaagct     60
cccaaccaag ctctcttgag gatcttgaag gaaactgaat tcaaaaagat caaagtgctg   120
ggctccggtg cgttcggcac ggtgtataag gtaaggtccc tggcacaggc ctctgggctg   180
ggccgc                                                              186

<210> SEQ ID NO 9
<211> LENGTH: 19
<212> TYPE: DNA
<213> ORGANISM: Artificial Sequence
<220> FEATURE:
<223> OTHER INFORMATION: synthetic

<400> SEQUENCE: 9
tgcacctacg ggcctaaga                                                 19

<210> SEQ ID NO 10
<211> LENGTH: 20
<212> TYPE: DNA
<213> ORGANISM: Artificial Sequence
<220> FEATURE:
<223> OTHER INFORMATION: synthetic

<400> SEQUENCE: 10
ccttcgcatg aagaggccga                                                20

<210> SEQ ID NO 11
<211> LENGTH: 20
```

```
<212> TYPE: DNA
<213> ORGANISM: Artificial Sequence
<220> FEATURE:
<223> OTHER INFORMATION: synthetic

<400> SEQUENCE: 11
caggagaggg agggactctg                                              20

<210> SEQ ID NO 12
<211> LENGTH: 22
<212> TYPE: DNA
<213> ORGANISM: Artificial Sequence
<220> FEATURE:
<223> OTHER INFORMATION: synthetic

<400> SEQUENCE: 12
atcgaggatt tccttgttgg ct                                           22

<210> SEQ ID NO 13
<211> LENGTH: 20
<212> TYPE: DNA
<213> ORGANISM: Artificial Sequence
<220> FEATURE:
<223> OTHER INFORMATION: synthetic

<400> SEQUENCE: 13
acggggacca gacaactgta                                              20

<210> SEQ ID NO 14
<211> LENGTH: 20
<212> TYPE: DNA
<213> ORGANISM: Artificial Sequence
<220> FEATURE:
<223> OTHER INFORMATION: synthetic

<400> SEQUENCE: 14
atgaagaggc cgatccccag                                              20

<210> SEQ ID NO 15
<211> LENGTH: 19
<212> TYPE: DNA
<213> ORGANISM: Artificial Sequence
<220> FEATURE:
<223> OTHER INFORMATION: synthetic

<400> SEQUENCE: 15
gatcggcctc ttcatgcga                                               19

<210> SEQ ID NO 16
<211> LENGTH: 20
<212> TYPE: DNA
<213> ORGANISM: Artificial Sequence
<220> FEATURE:
<223> OTHER INFORMATION: synthetic

<400> SEQUENCE: 16
ggccatcacg taggcttcat                                              20
```